(12) United States Patent
Lihme et al.

(10) Patent No.: US 6,620,326 B1
(45) Date of Patent: Sep. 16, 2003

(54) EXPANDED BED ADSORPTION SYSTEM

(75) Inventors: Allan Otto Fog Lihme, Birkerød (DK);
René Oehlenschlæger, Copenhagen (DK); Brian A. Olsen, Albertslund (DK); Elias Zafirakos, Copenhagen (DK)

(73) Assignee: Upfront Chromatography A/S, Copenhagen (DK)

( * ) Notice: Subject to any disclaimer, the term of this patent is extended or adjusted under 35 U.S.C. 154(b) by 0 days.

(21) Appl. No.: 09/719,781

(22) PCT Filed: Jun. 18, 1999

(86) PCT No.: PCT/DK99/00336
§ 371 (c)(1),
(2), (4) Date: Mar. 12, 2001

(87) PCT Pub. No.: WO99/65586
PCT Pub. Date: Dec. 23, 1999

(30) Foreign Application Priority Data

Jun. 18, 1998 (DK) .......................................... 1998 00828

(51) Int. Cl.⁷ .............................................. B01D 15/08
(52) U.S. Cl. ..................... 210/635; 210/656; 210/198.2
(58) Field of Search .................. 210/635, 656, 210/659, 198.2, 502.1

(56) References Cited

U.S. PATENT DOCUMENTS

| 4,780,113 A | * | 10/1988 | Koslow | 210/656 |
| 5,522,993 A | * | 6/1996 | Carlsson | 210/656 |
| 5,759,395 A | * | 6/1998 | Hagerlid | 210/269 |
| 5,935,442 A | | 8/1999 | Lihme et al. | |
| 6,193,883 B1 | * | 2/2001 | Kroner | 210/198.2 |
| 6,224,761 B1 | * | 5/2001 | Tanimura | 210/198.2 |

FOREIGN PATENT DOCUMENTS

| WO | WO9520427 | 5/1995 | ................. 210/656 |

OTHER PUBLICATIONS

Snyder Introduction to Modern Liquid Chromatography 1979, pp. 216–217.*
Hjorth, Trends in Biology, vol. 15, No. 6, (1997) pp. 230–235.
Thommes et al., Journal of Chromatography A, vol. 752, Nos. 1–2, p. 111–122 (1996).
Bjorklund et al., Journal of Chromatography A, vol. 743, No. 1, pp. 145–162 (1996).
Kaufmann, Journal of Chromatography B, vol. 699, Nos. 1–2, pp. 347–369 (1997).
Hjorth,R. et al.; "Analysis of some operating parameters. . ."Bioseparation 5: 217–223, 1995.

* cited by examiner

Primary Examiner—Ernest G. Therkorn
(74) Attorney, Agent, or Firm—Birch, Stewart, Kolasch & Birch, LLP

(57) ABSTRACT

The present application describes various improvements and further developments to the Expanded Bed Adsorption (EBA) technology. In particular, the application describes an EBA process where elution is performed in fluidized mode, i.e., in expanded bed mode, the so-called All Expanded Process. This improvement which is based on the use of controlled density particles, e.g., particles having a density of at least 1.3 g/ml, provides valuable advantages with respect to use of reduced amounts of elution buffer.

6 Claims, 18 Drawing Sheets

SEEN FROM ABOVE

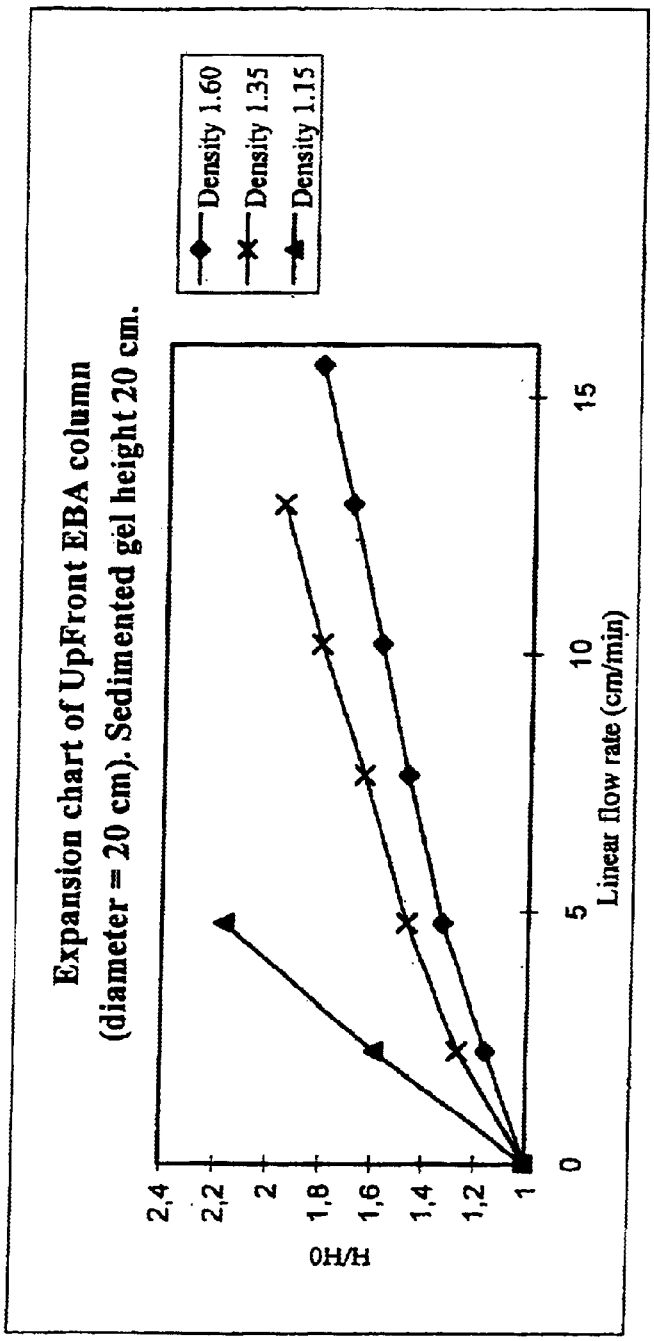
FIGURE A1

EXPANDED BED ADSORPTION SYSTEM

This application is the national phase under 35 U.S.C. §371 of PCT International Application No. PCT/DK99/00336 which has an International filing date of Jun. 18, 1999, which designated the United States of America.

FIELD OF THE INVENTION

EBA is an abbreviation for Expanded Bed Adsorption. This is a technology used within the pharmaceutical and diagnostic industries for the purification of, i.a., proteins and peptides from a vast variety of extracts and raw materials. The present invention relates to various improvements for the known EBA technology.

BACKGROUND OF THE INVENTION

A traditional purification process for a mixture comprising one or several target molecules could be purification on a packed column (i.e. not EBA), however this requires multiple operational steps such as filtration and centrifugation and a number of steps in order to ensure that impurities and particles are removed before the mixture is applied to a suitable packed column. These steps are necessary in order to avoid that the packed column clogs up. In the packed column, a given chromatographic medium is present for binding of the molecule(s) which are the target for the purification. This chromatographic medium can be adapted to various purification purposes.

The main principle in EBA is to keep the chromatographic medium fluidised and thereby also allow particles to pass through the column. By using the EBA technology, it is in many instances possible to avoid the above-mentioned operational steps before application of the raw material to the column. In this manner, time and expenses for these processes are reduced making EBA a valuable technology which is economically recommendable for the purification of a countless number of molecules. It reduces time and expenses for a lot of equipment.

In order to utilise the EBA technology, an EBA column and a suitable chromatographic medium should be used.

A brief presentation of the steps used in the EBA technology will be given in the following.

1. An adequate quantity of chromatographic medium is placed in an EBA column.
2. A flow through the medium from below and up through the medium is initiated. The medium is fluidised.
3. The medium is rinsed in the column and the salt concentration and pH are set.
4. Raw material is applied. The medium binds the target molecule(s).
5. Remaining raw material is rinsed out from the column.
6. The column is packed. The matrix is sedimented.
7. The liquid above the medium is drained.
8. The target molecule is eluted off the medium.
9. Rinsing and regeneration of the chromatographic medium (optionally).

Steps 1-5 and 9 are implemented in expanded bed mode. In step 6, the flow has stopped, in step 7, liquid is drained through the bottom, and in step 8, the flow comes from above and down, i.e. in packed mode.

Before the raw material is applied to the column, it should be ensured that the expansion is stable. This can be done visually or by determining the theoretical bottoms ("Expanded Bed Adsorption" by Pharmacia Biotech, page 14). A double determination must not deviate by more than 20%. During visual inspection, any channels and jet streams are located. If the medium moves in small circles, and local jet streams and channels are not observed, it is considered to be stably expanded. By the term jet streams is understood a clear stream of liquid and thus medium locally in the EBA column. If the jet stream flows upwards at one place, it will typically flow downwards at another. Further information about EBA technology can be found in the book "Expanded Bed Adsorption" by Pharmacia Biotech.

The Chromatographic Medium

In EBA technology, only density controlled particles which can adsorb a given target molecule are used. Density and diameter of the medium determine the extent of the flow to which the particles can be exposed without being flushed out of the column. The particles used are preferably round. The diameter is proportional to the square of the fall velocity. This means that two spheres of equal density will not necessarily fall at the same velocity. The fall velocity is proportional to the difference of density between the liquid and the material of which the sphere is produced to the power of one, demonstrating the great significance of the diameter.

In liquid chromatography at low pressure, many types of chromatographic medium are used. These media may either have a higher density than the surrounding liquid in which case the medium will precipitate, or a lower density than the surrounding liquid in which case the medium will float. One example of these density modified particles and their application in fluidised columns is described in WO 92/00799.

In packed column chromatography, a medium which is not density controlled is employed. In practice, water will be led into the top of the column so that the liquid flows from above and down. The medium will move in the same direction as the liquid flow. At the same time, the quantity of the medium is limited as the medium at a given point will pack so hard that the liquid cannot flow freely. Another factor determining whether the medium will pack down hard or not is the velocity at which liquid is led through the column, i.e. the liquid flow.

DKIEP 0538350 T3 discloses chromatographic adsorption particles having covalently bound thereto at least one active substance for binding of molecules in a liquid chromatographic liquid bed process. These adsorption particles are formed of a porous composite material with pores permitting access for the said molecules to the interior of the composite material. The spheres can be produced having a given density and diameter. The density is controlled by incorporation of one or more inert particles in the chromatographic medium, the number, material and percentage of the inert particles being significant for the ultimate density of the chromatographic medium. In addition, the pore size can be controlled. The density controlled particles can be viewed as inert heavy/light particles coated with a hydrophilic layer, a conglomeration compound such as an agarose layer of different concentration and thus pore size. See FIG. 1a for two examples of the described spheres. Here, two types of products which are marketed today are shown. The Streamline matrix by Pharmacia Biotech, Sweden, and the UpFront Matrix by UpFront Chromatography A/S, Denmark. These have been produced according to the same principle with one or more particles inside a sphere of agarose.

The book *"Expanded Bed Adsorption"* by Pharmacia, Sweden, discloses that the size and density of the individual sphere at a given flow situates the sphere at a specific position in the column. The small and light spheres will move to the upper part of the expanded matrix while large, heavy particles will move towards the lower part. The result is that the particles settle at their ideal position after a suitable period of time. When this has taken place, expansion will be stable.

Columns

DK/EP 0538350 T3 discloses a liquid bed reactor as a down/upflowing liquid fluid bed reactor comprising a vertical reactor container with an inlet, an outlet, a fluidised particle bed of chromatographic adsorbent particles and means for initiating movement which are located near by or in the fluidised particle layer which is closest to the liquid inlet. There is a mixed zone, i.e. a stirring zone, the size of which is determined by the degree of stirring, the liquid flow and the quantity of matrix in the reactor container. Above/below this zone is a non-mixed zone in which a so-called plug flow is achieved. By the term plug flow is understood a movement of the liquid as a band through the container and consequently also through the matrix.

An example of such a reactor container is an UpFront column 20™ which is an upflow reactor developed by UpFront Chromatografy A/S, Copenhagen, Denmark. See FIG. 1 and 2 for the construction thereof and examples of application in fluidised and packed mode, respectively.

This reactor container is constructed in such a manner that a supporting net with a pore size of 50 $\mu$m is located at the bottom. Below the supporting net is an outlet/inlet which is primarily used as an outlet during elution. A motor axis on which a stirrer is secured extends down the middle of this net. The rate of the stirrer can be varied. Stirring only occurs when the flow comes up through the column. During elution the stirrer is stopped. Right above the supporting net is a side inlet located. Here, all liquid is supplied when the matrix is to be and has been fluidised. This inlet can be opened and closed by sliding the inlet valve into or out of the column pipe. The column pipe is a borosilicate pipe of 20 mm. The actual inflow takes place through four round openings with a diameter of 3 mm each located in that part of the inlet valve which is inside the column pipe. The valve is closed at the end and the four round openings are distributed in the same cross-section in two axes placed at an angle of 90 degrees to each other. The column pipe is 50 cm long (high) and on its side is a scale so as to enable reading of the expansion of the matrix at any time. In addition, the column is provided with a float adapter, an UpFront float, which provides a gentle and good distribution of the elution buffer during elution. At the top is an outlet/inlet. Every inlet and outlet is provided with valves on which suitable hoses are mounted. Buffer and raw materials are pumped into the column at an even flow. Typically, the matrix will be ⅓ of the column height. In this case, it is possible to expand up to 3 times. Depending on the type of particles/matrix applied, the flow can vary from 6 column cm/min to 900 column cm/min.

The stirring zone varies from 2–20 cm. In this application the term stirring zone is to be understood as exactly the height in the column at which a stirring of liquid and matrix occur. The viscosity and flow of the liquid and the stirrer's design and rate are significant for the extent of the zone. In addition, it is important that the column is plumb. This concept can also be upscaled to a larger column diameter.

WO 95/20427 discloses a construction for adsorption/desorption of a substance where liquid can flow through a column of matrix. This construction comprises: a) a bottom adapter which is located at the bottom part of the container. The bottom adapter defines the bottom. The adapter has an opening in the bottom for inflow/outflow of liquid to and from the bottom part of the container. This adapter also has a distribution function. It creates the back pressure necessary to create plug flow, b) a top adapter which is located at the top part of the container. This adapter has an opening pointing towards the bottom for inflow/outflow of liquid to and from the top part of the container. It also has a distribution function. This upper adapter has a density permitting that it floats on the liquid passing through the container. By means of hoses, both adapters can lead liquid to and from the container depending on the direction in which the liquid should flow.

Pharmacia Biotech has developed an EBA column which distributes the liquid in another way than by stirring. In the bottom of the column there is an inlet/outlet. Above the column is a distribution plate through which the liquid has to pass to enter the column. The distribution plate creates the pressure drop necessary to create a plug flow. By the term plug flow is understood the movement of the liquid as one front through the matrix. This bottom adapter leads the liquid vertically upwards through the column. The top adapter can be positioned anywhere necessary in the column. In this manner head space can be reduced. By the term head space is understood the liquid above the matrix.

BRIEF DESCRIPTION OF FIGURES

FIG. 1 illustrates an EBA column in fluidised mode. There are two connecting branches (openings) at the bottom part of the column, one in the side and one in the bottom below the supporting net. They are used for the inflow and outflow of liquid respectively. One connecting branch (opening), i.e. inlet, is situated above the supporting net and is used to supply liquid when the column is used in fluidised mode. The other connecting branch (opening) is situated below the supporting net (which may have a pore size of e.g. 50 $\mu$m) and is applied during elution. A chromatographic medium which is fluidised in the example shown by means of a liquid flow from below and up is shown in the column. At the upper part of the column an UpFront float floats. This float is primarily used during the elution process. At the top is a common outlet/inlet. The black arrows indicate the flow direction in the example shown. In addition, head space is the liquid between the top of the expanded matrix and the top of the fluid; in the example shown, this is upto below the UpFront float. However, there is some liquid around this which can be ignored. The stirring zone is the zone where a distinct mixture of inflowing fluid/buffer and matrix occurs. Above this, the matrix is in stable expansion.

Here, examples of two different spheres used for EBA are shown:

Expanded Bed Matrices

|  | (a) Streamline matrix | (b) UpFront matrix |
| --- | --- | --- |
| Composition: | Agarose/quartz | Agarose/glass beads (20% v/v) |
| Structure: | Conglomerate of many small grains | Pellicular structure with only one glass bead in the center |

-continued

|  | (a)<br>Streamline matrix | (b)<br>UpFront matrix |
|---|---|---|
| Size: | 100–300 μm | 100–300 μm |
| Density: | 1.1–1.2 g/ml | 1.3–1.5 g/ml |

FIG. 2

Figure 1:
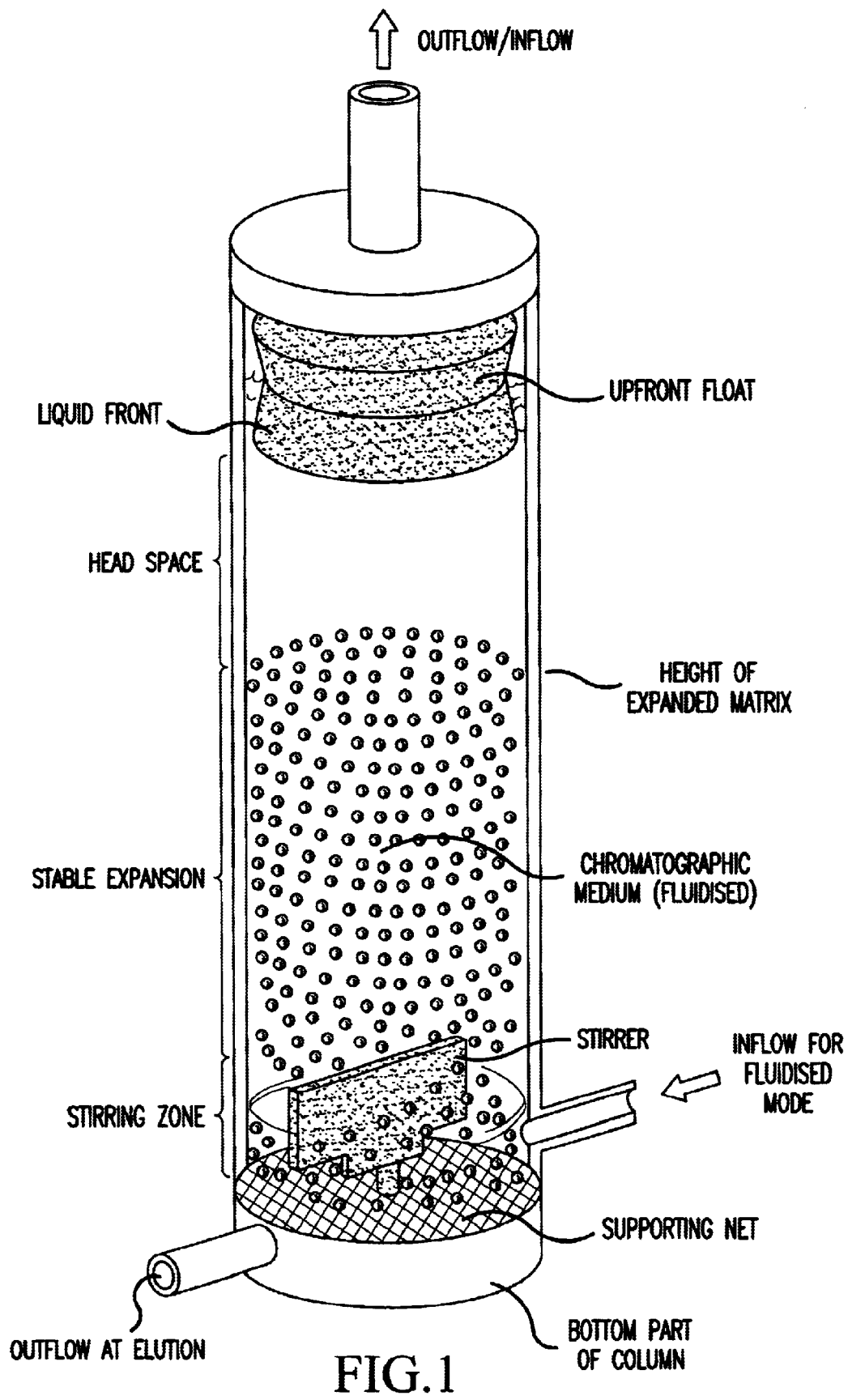
FIG. 1
Figure 1A:
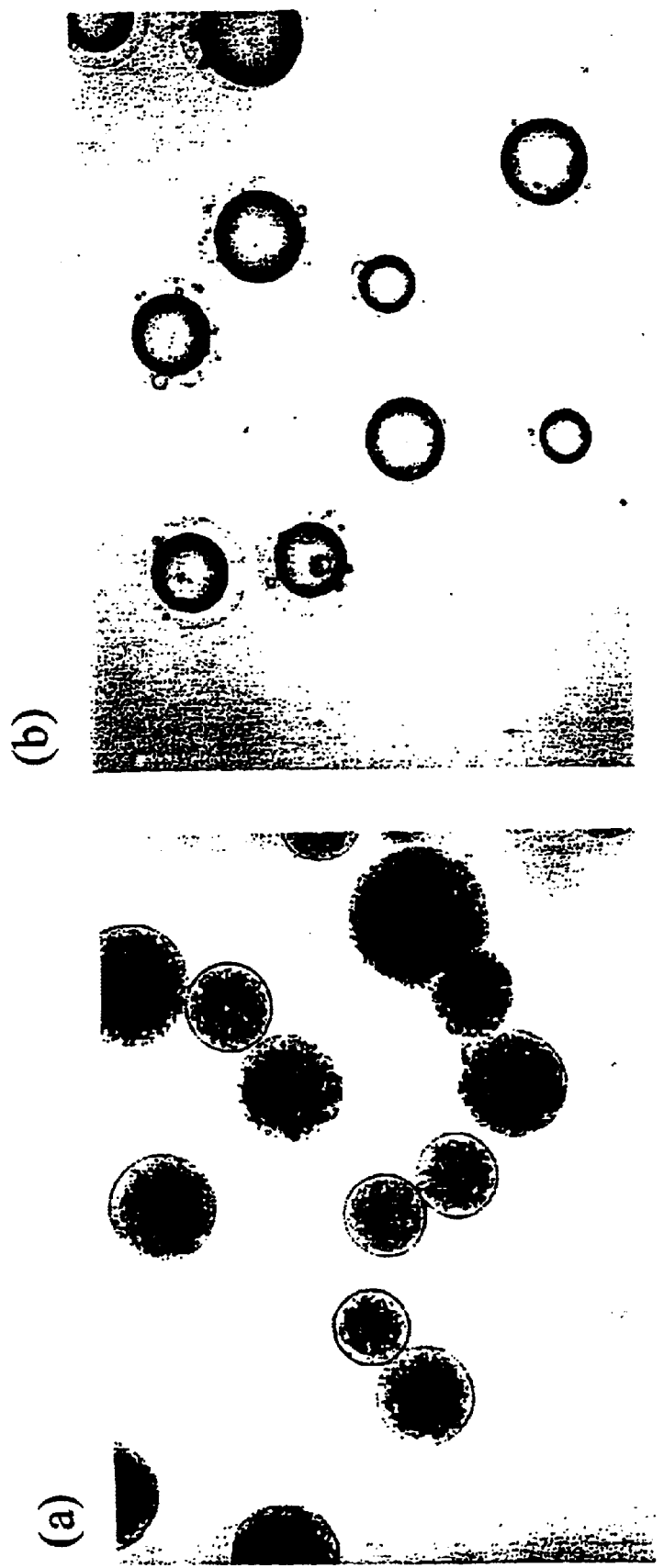
FIG. 1A
Figure 2:
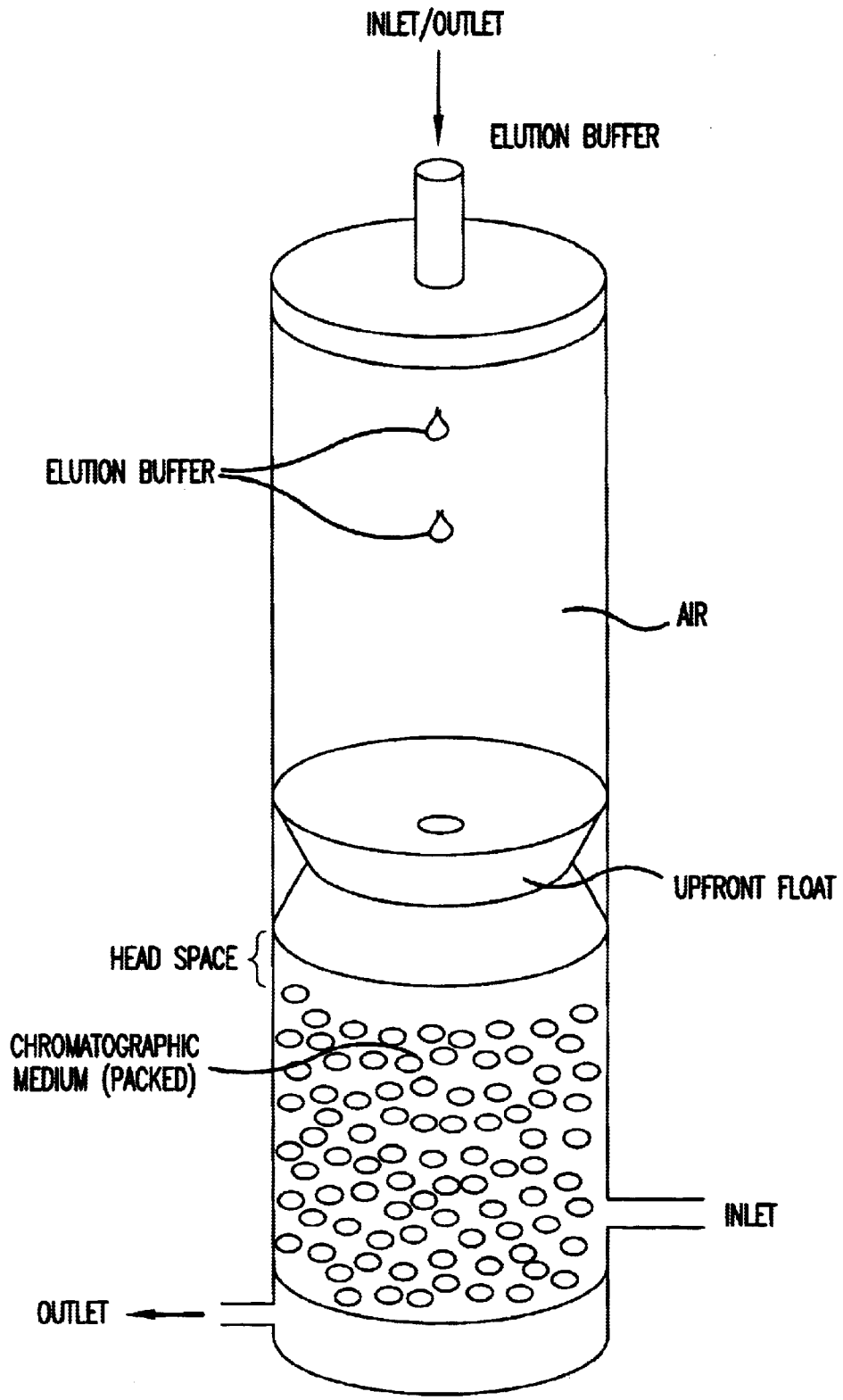

Here, the same column as in FIG. 1 is shown, however in packed mode. Now, the flow has reversed and packed mode is implemented. Elution is taking place. The liquid flows in at the top and out at the bottom. Right above the top of the packed chromatographic medium, an UpFront float rests on the elution fluid. This float is used during the elution process for distribution of the inflowing liquid across the matrix. Below the UpFront float is a small head space. The stirrer and the support net cannot be seen as it is hidden in the chromatographic medium. The stirrer must be turned off during elution. Above the UpFront float is gas. The arrows indiciate the flow direction.

FIG. 3

Figure 3:
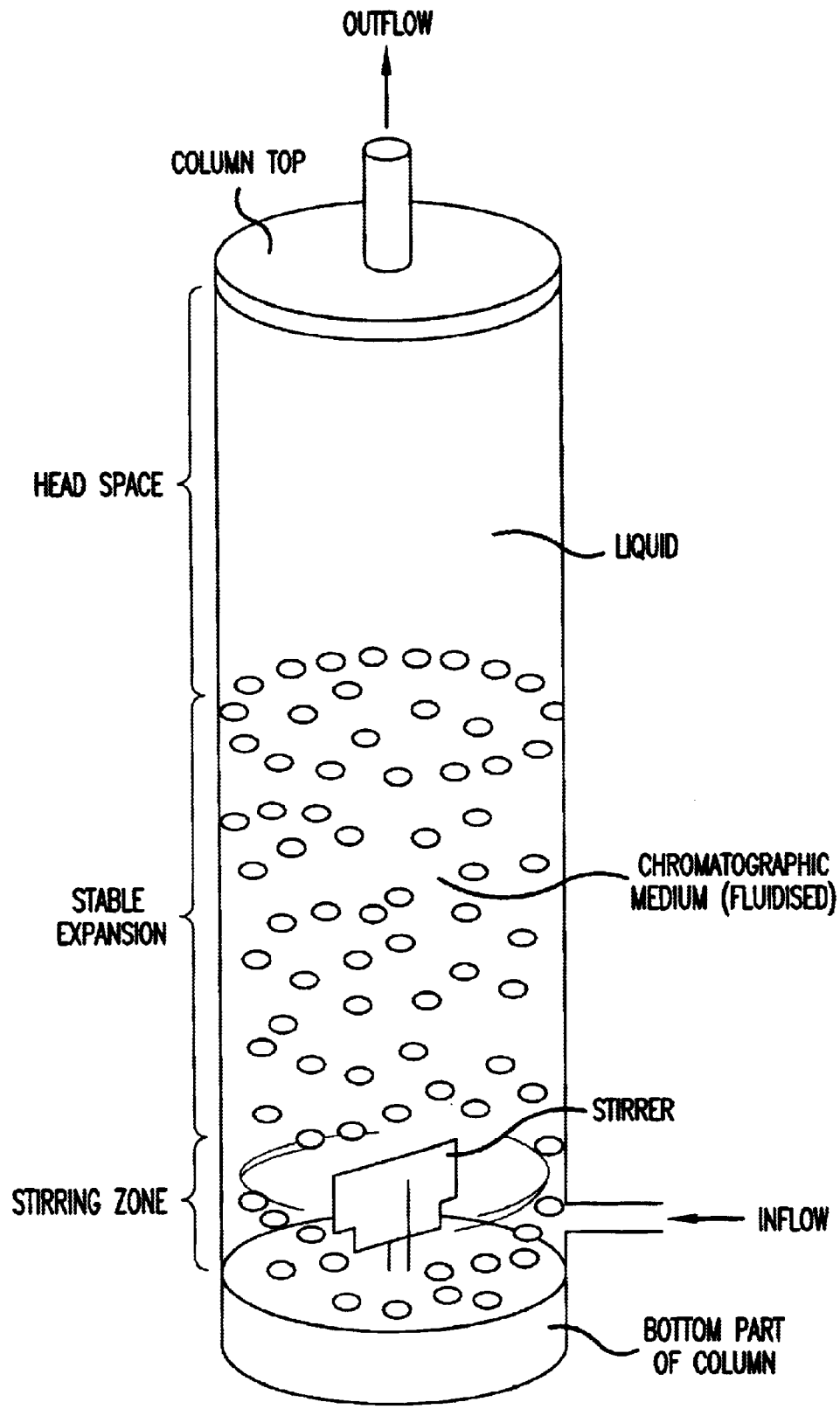

FIG. 3 shows the fundamental construction of an EBA column to be used in the All expanded process. In the figure one inlet in the bottom part approximately next to the stirring body and one outlet at the top are shown. In this case, the stirrer is located at the bottom. The construction of the stirrer itself may be varied if required (see below). The arrows indicate the flow direction.

FIG. 4

Figure 4:
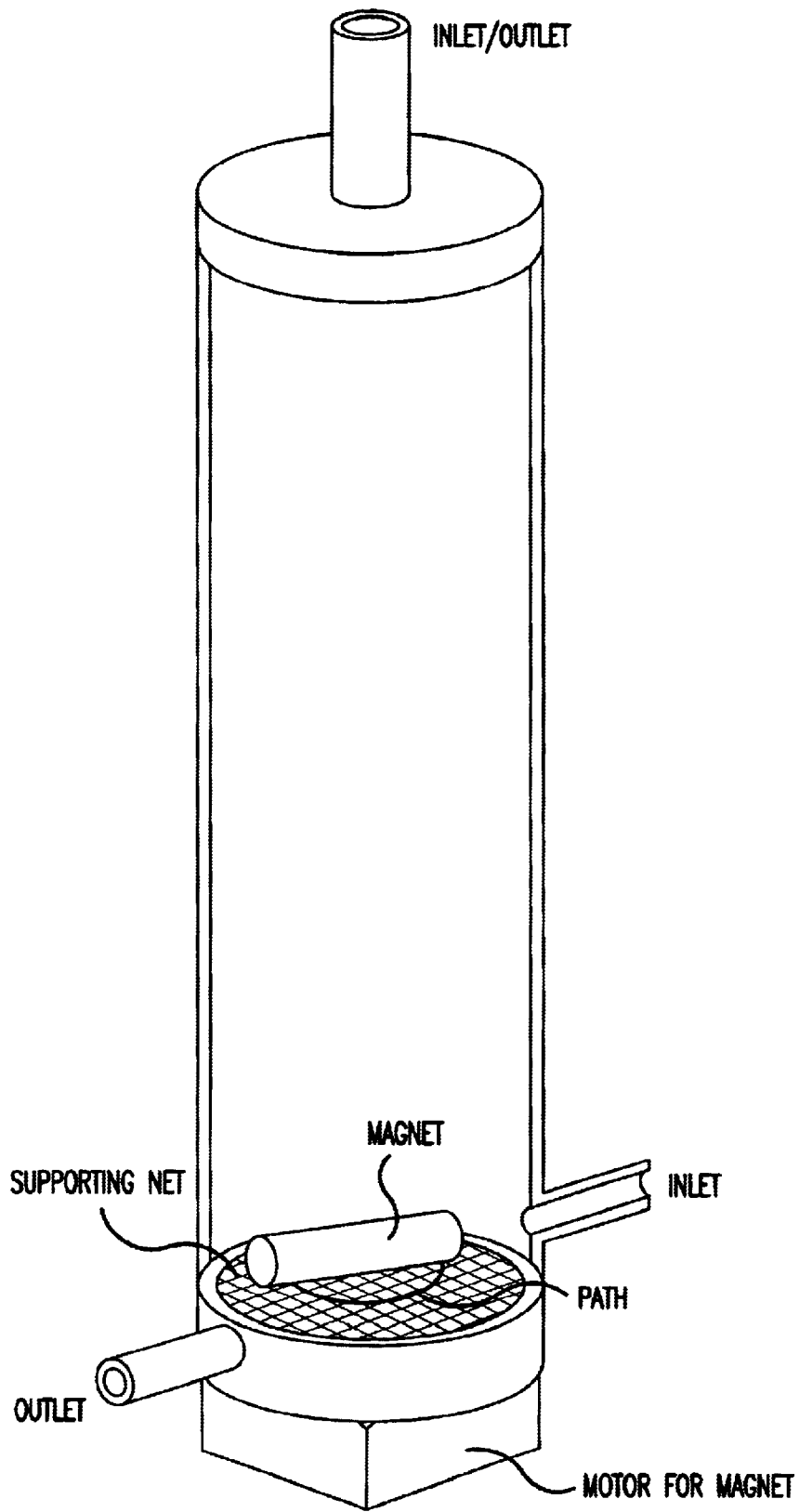

FIG. 4 shows an EBA column with a supporting net and two openings at the bottom part. An inlet above and an outlet below the supporting net. The column can be used for normal EBA elution (packed column) and the all expanded process. A path of a suitable material is cast on the supporting net in order that magnetic stirring does not expose the net to wear. Here, the magnet is shown as being round and cylinder shaped and is situated at the bottom on top of the supporting net. The magnet can be designed in several ways, e.g. as shown below.

FIG. 4A

Figure 4A:
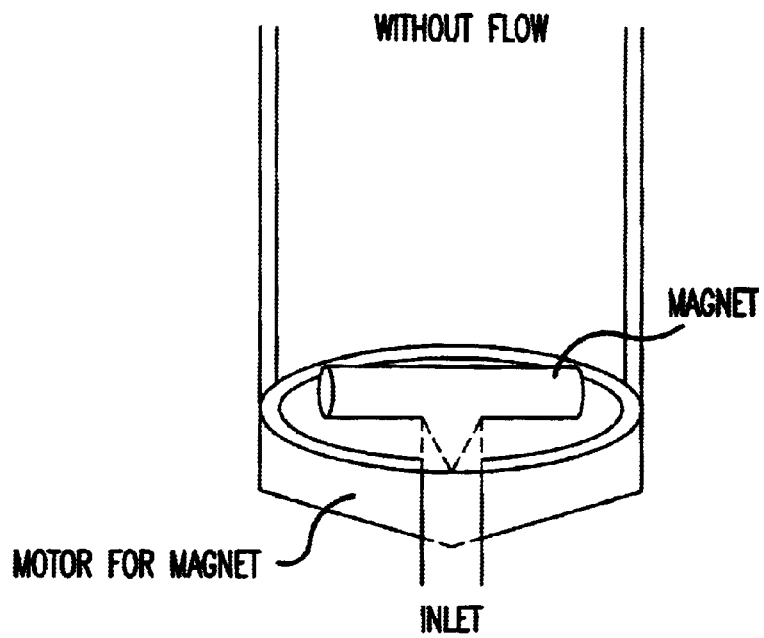
Figure 4B:
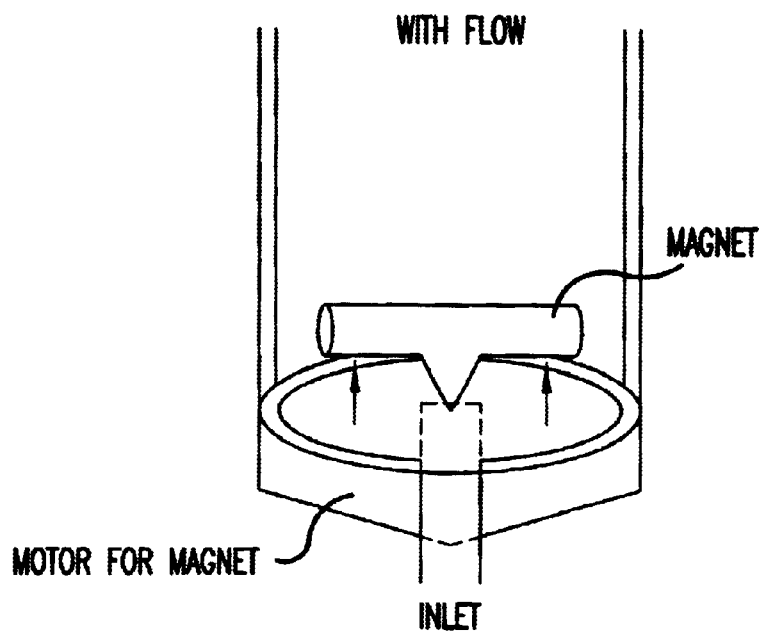

FIG. 4a takes the all expanded process of the invention into account and is thus constructed without a supporting net and with only one opening in the bottom. The magnet acts as a shut-off valve/plug, only by flow from below is the magnet lifted. Here, it is shown without flow.

FIG. 4B

As FIG. 4A but with flow. The wedge/cone-shape of the underside of the magnet also contributes to stabilising the magnet and preventing the magnet from suddenly coming off which could cause damage of the column. The axle controlled stirring has been replaced by magnetic stirring.

FIG. 5

Here, a bird's-eye view of a possible construction of a magnet with eight wings is shown. Example of magnet with four axles.

FIG. 6

Figure 6:
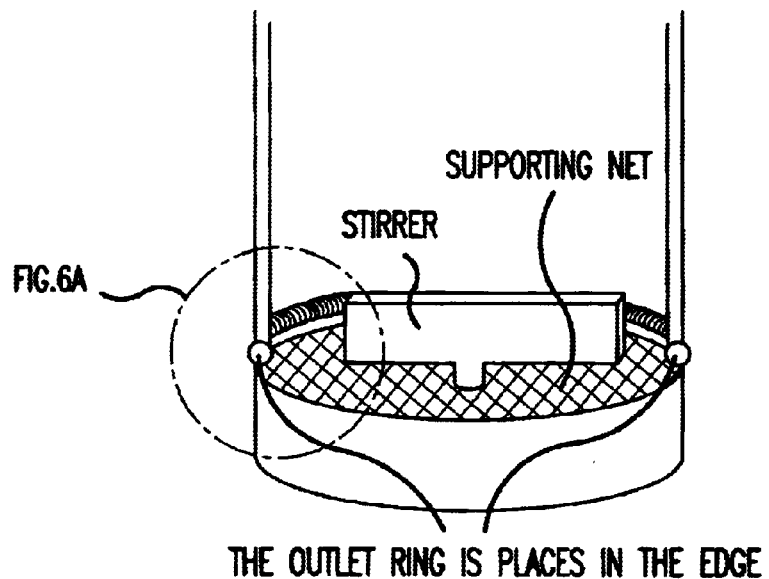
Figure 6A:
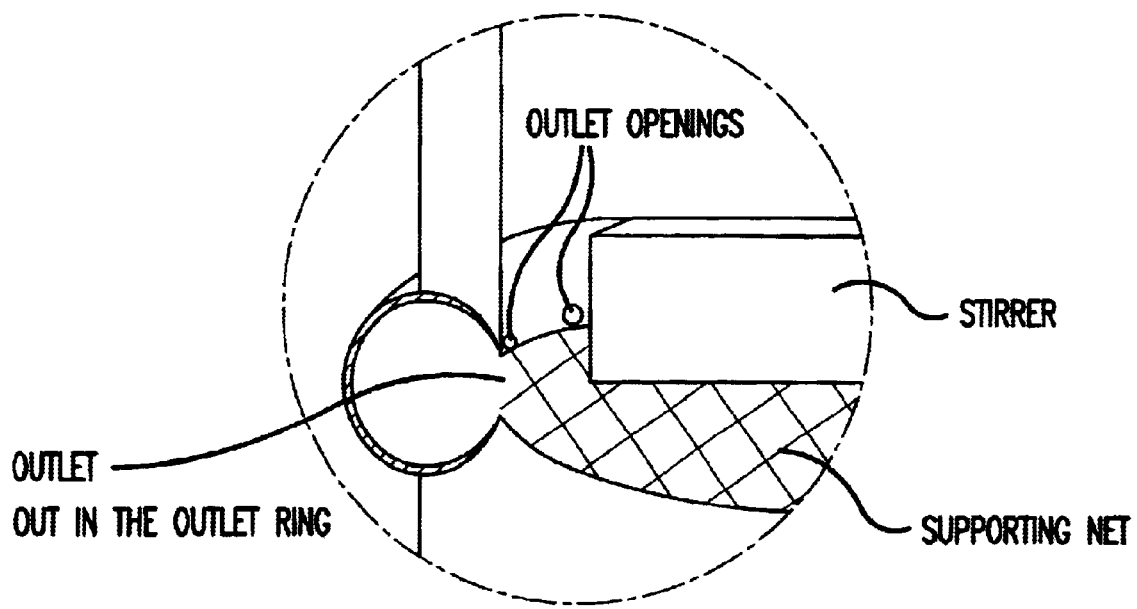

FIG. 6 illustrates the location of a possible construction of an inlet ring. It has been placed right at the side to avoid the presence of sedimented gel on the outer side. The outlet opening of the pipe is in line with the innerside of the column. The pipe is placed completely outside the diameter of the column. The distance between two diagonal outlet openings is equivalent to the column diameter. In the figure, the bottom part of an EBA column is shown. A magnification of the actual location of the inlet ring with three outlet openings is shown.

Figure 7A:
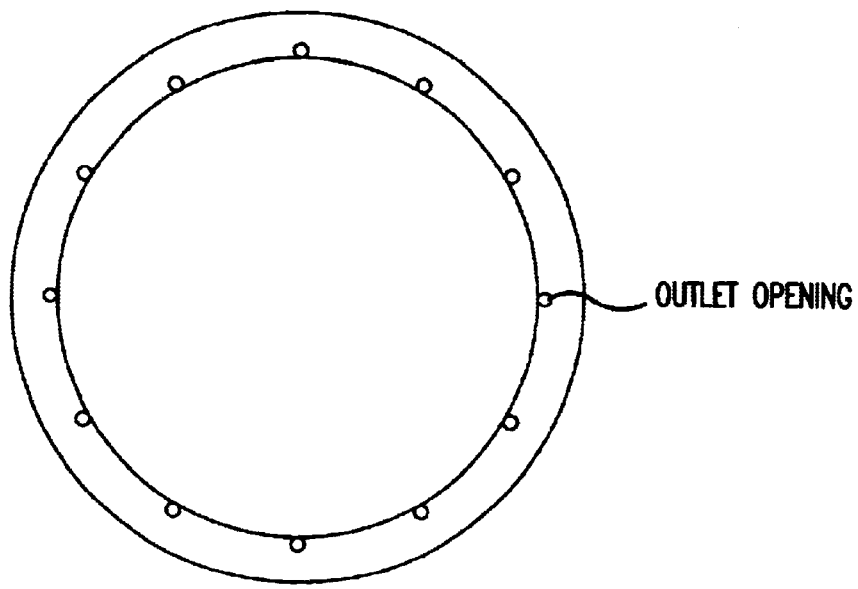
Figure 7B:
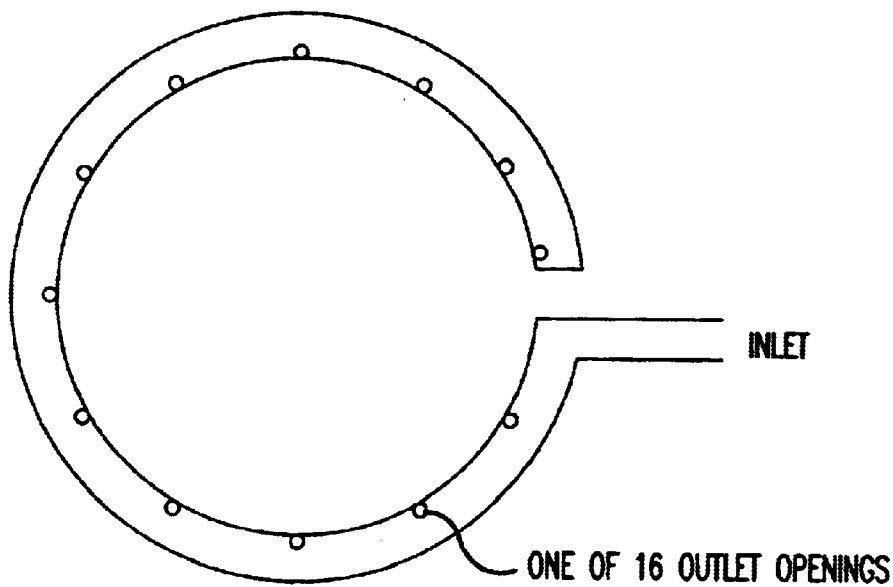

FIGS. 7A and 7B

Here, two possible constructions of inlet rings are shown.
a) The liquid flows in from the bottom, not shown, and all the way round.
b) The liquid flows in from the side. In this case, it is important that the liquid cannot flow all the way round back to the inlet.

FIG. 8

Figure 8:
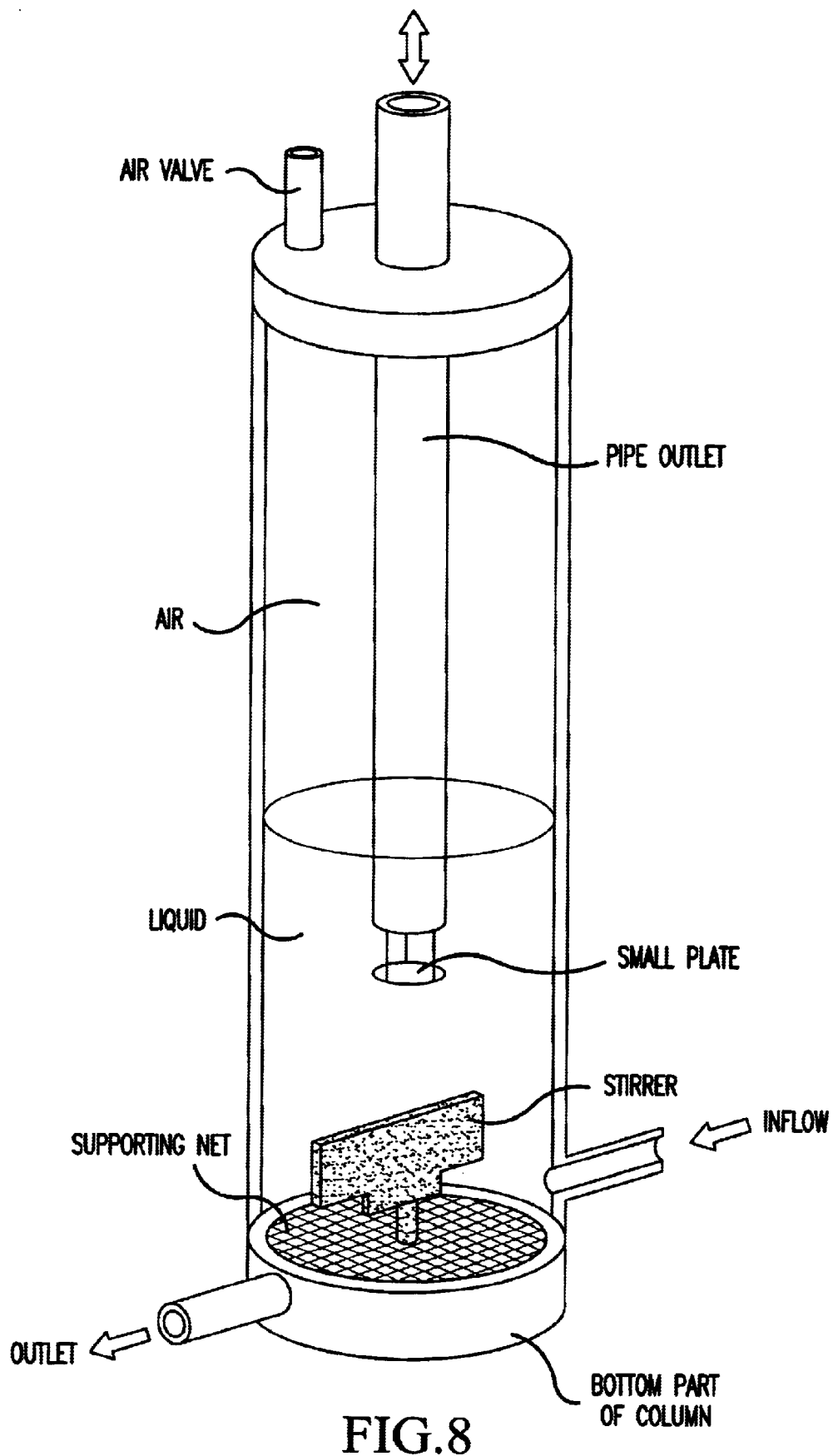

FIG. 8 corresponds to FIG. 4 but with another type of stirring. In addition, the outlet/inlet at the top of the column has been altered. Here, a possible construction of a mobile (adjustable) pipe in which the liquid can flow in or out is shown. In the top itself is an air valve to control the pressure in the chamber above the fluid. In the example shown, the liquid phase above the outlet opening can be reduced by increasing the pressure in the air space above the fluid.

FIG. 9

Figure 9:
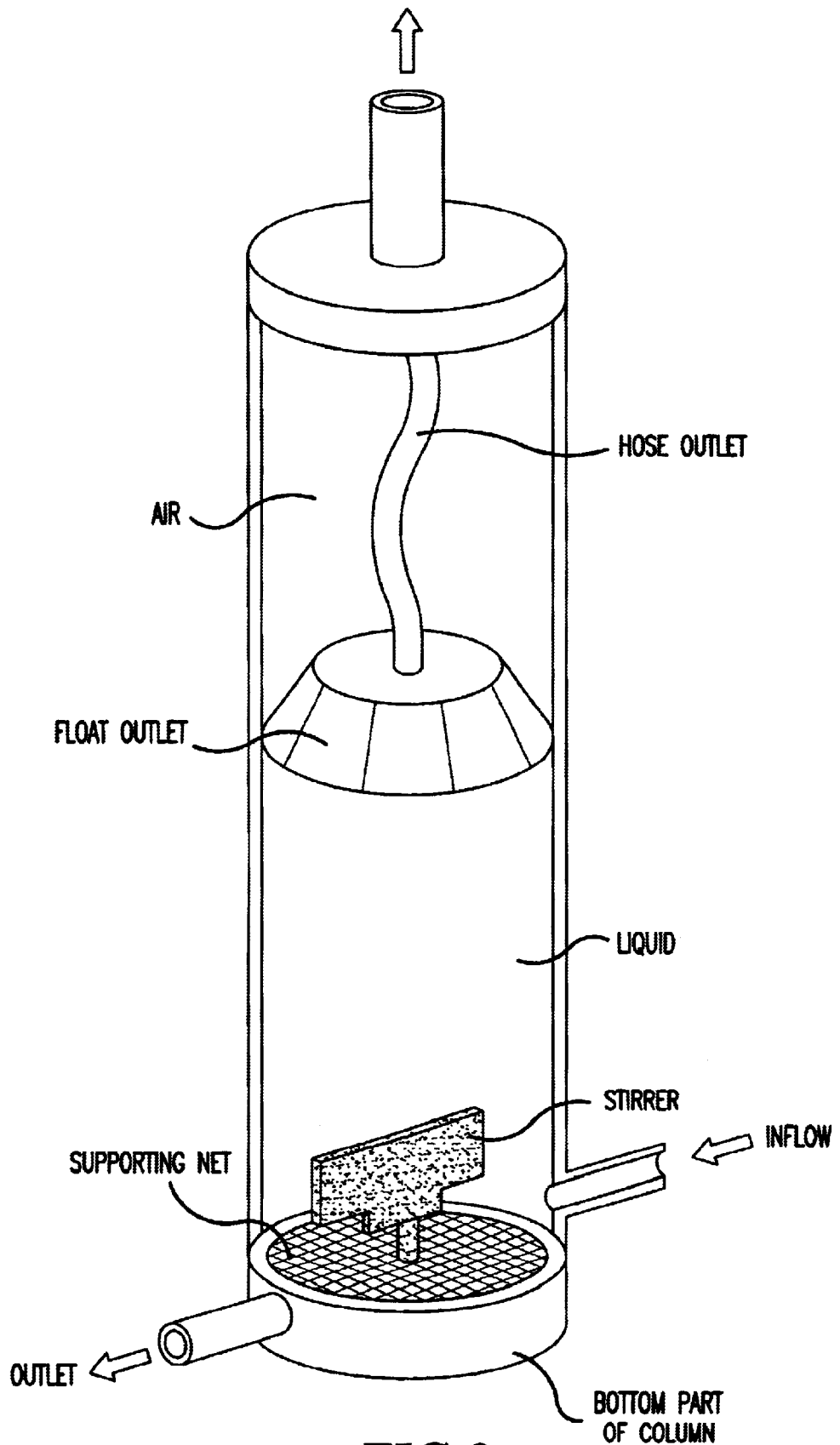

FIG. 9 shows an EBA column in principle as in FIG. 4 with an inlet above the supporting net and an outlet which is used during elution below the supporting net. An axle extends through the supporting net on which axle a stirrer unit is fixed. In the column, a floating outlet with a matching hose is placed at the top of the column. Above this floating outlet is a gas space.

FIG. 9A

A cross-section of the floating outlet of FIG. 9 showing the way in which this construction avoids "dead pockets".

FIG. 10

Figure 10:
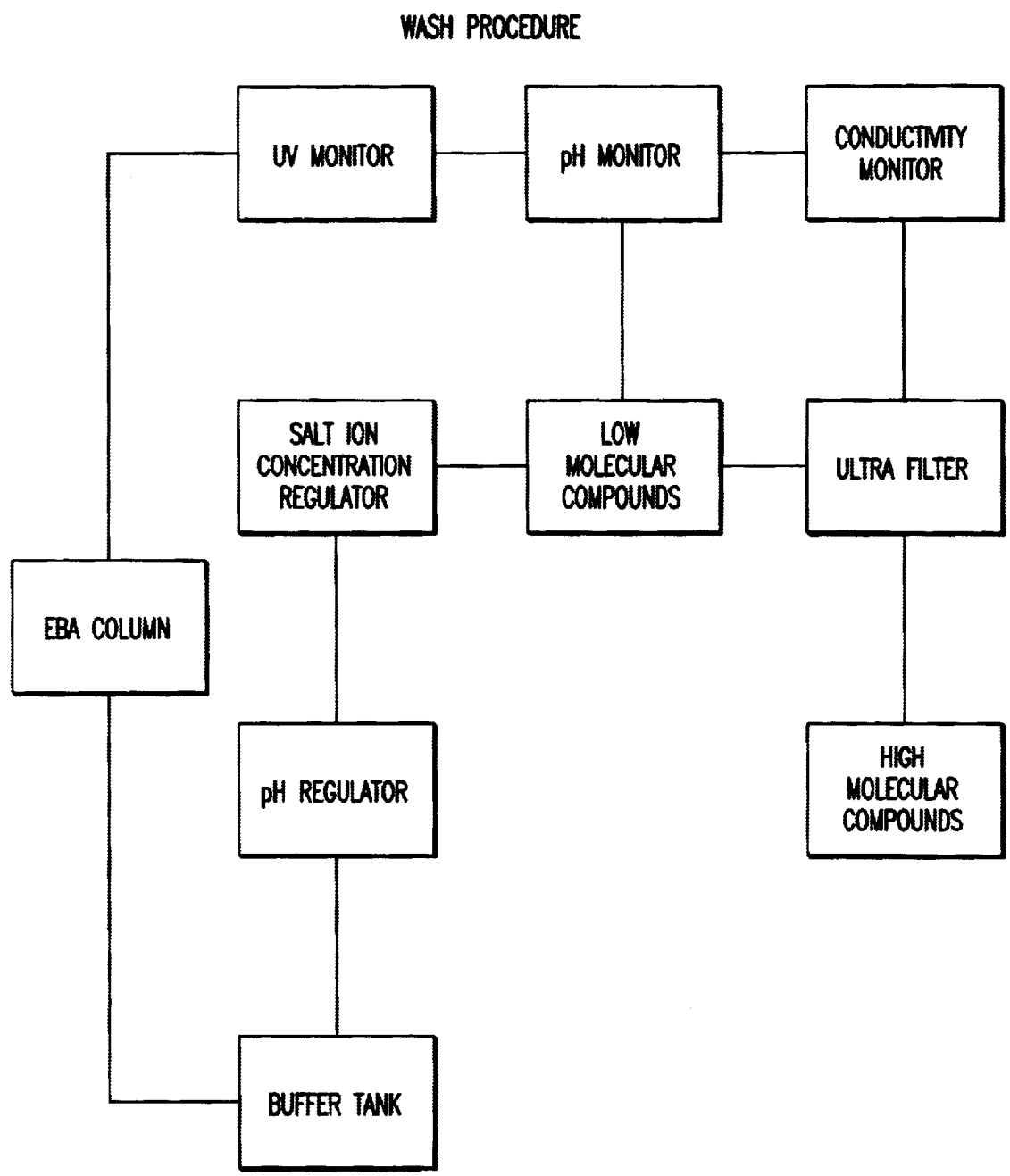

The system of FIG. 10 entails the application of the buffer liquid when it has passed through the column and three monitors to in-line ultra filtration. During ultra filtration the high-molecular substances will be separated from the liquid which then will flow through an in-line pH/salt ion concentration regulator. In this the desired pH and salt ion concentration are set. Then, the buffer is led back to the tank to be pumped through the column again. Some of the liquid is reused. However, some is lost with the high-molecular substances.

FIG. 10A

Figure 10A:
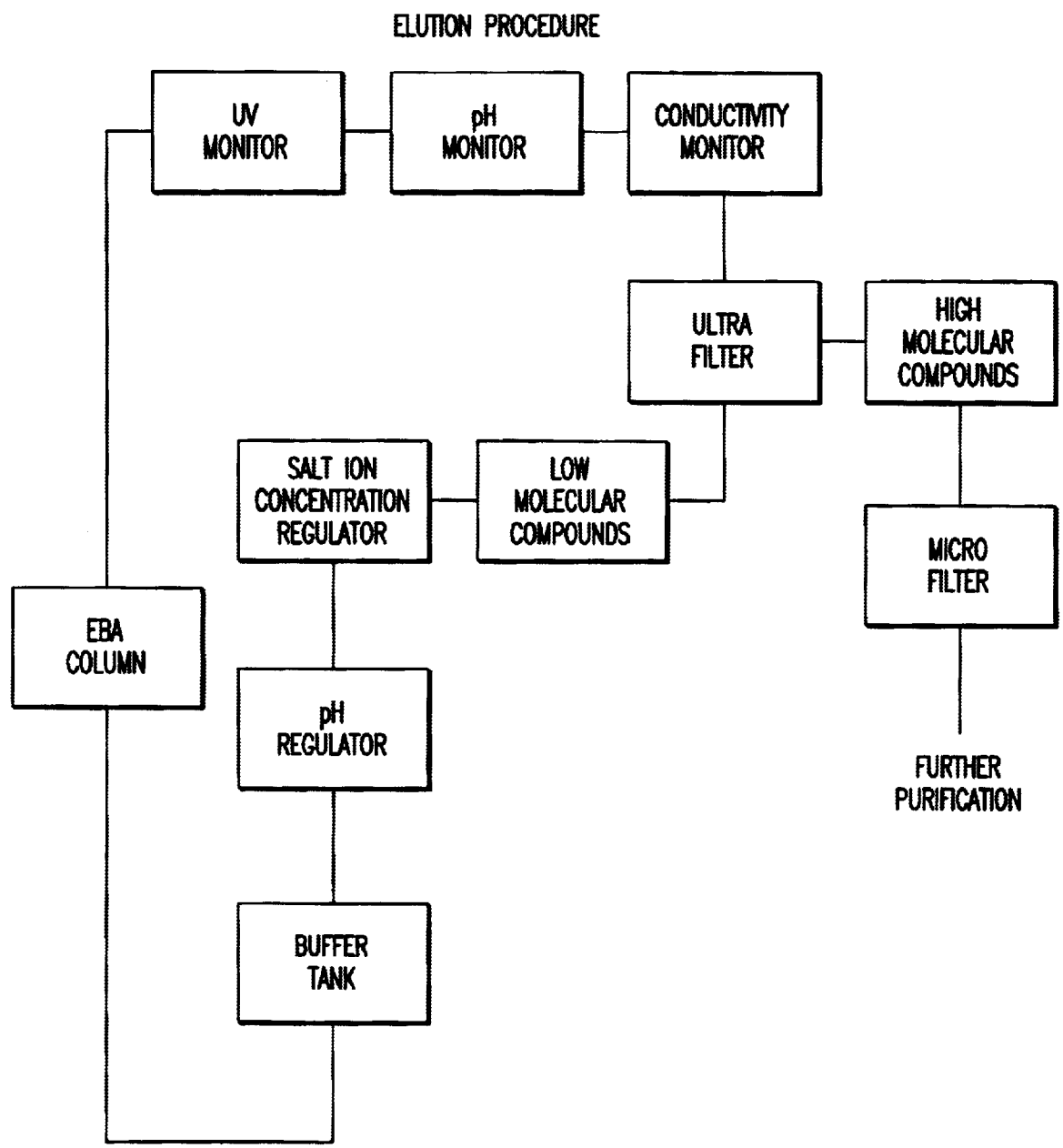

The system of FIG. 10A entails the application of the elution buffer when it has flown through the column and three monitors to in-line ultra filtration. During ultra filtration the target molecule will be separated (the target molecule is a high-molecular substance). It is passed on through a micro filter which is a coarser filter (compared to ultra filters) permitting the target molecule to pass for further purification and retaining e.g. bacteria. The liquid flowing through the ultra filter is led through the in-line pH/salt ion concentration regulator. In this the desired pH and salt ion concentration are set. Then the elution buffer is led back to the tank to be pumped through the column again.

FIG. 11

Cross-section of a chromatographic medium to be used in packed mode. Here, a glass sphere embedded in agarose is shown.

Figure 12:
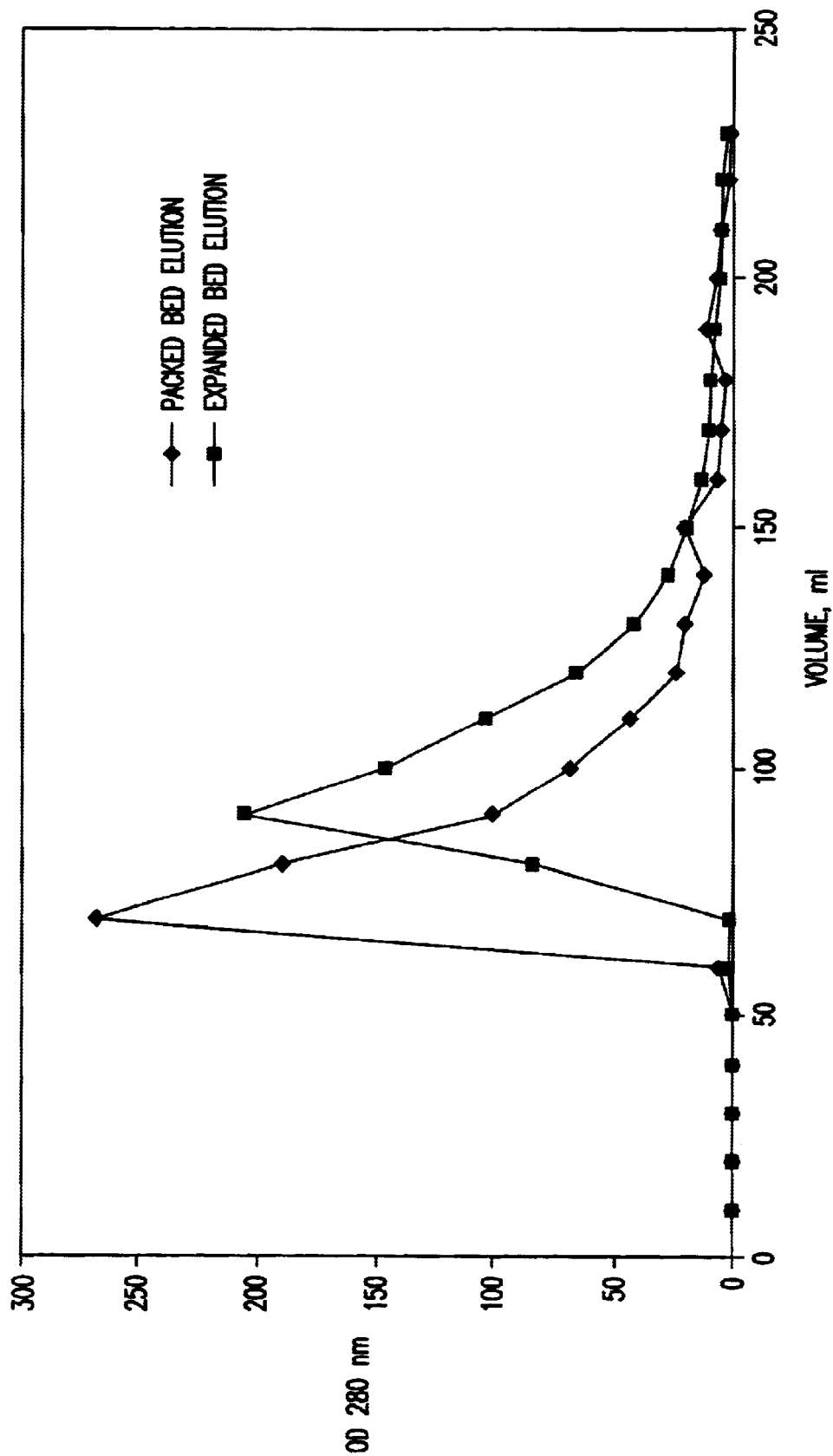

FIG. 12 shows a typical UV profile obtained as a result of the elution experiments. Linear flow rate 1 cm/min.

Figure 13:
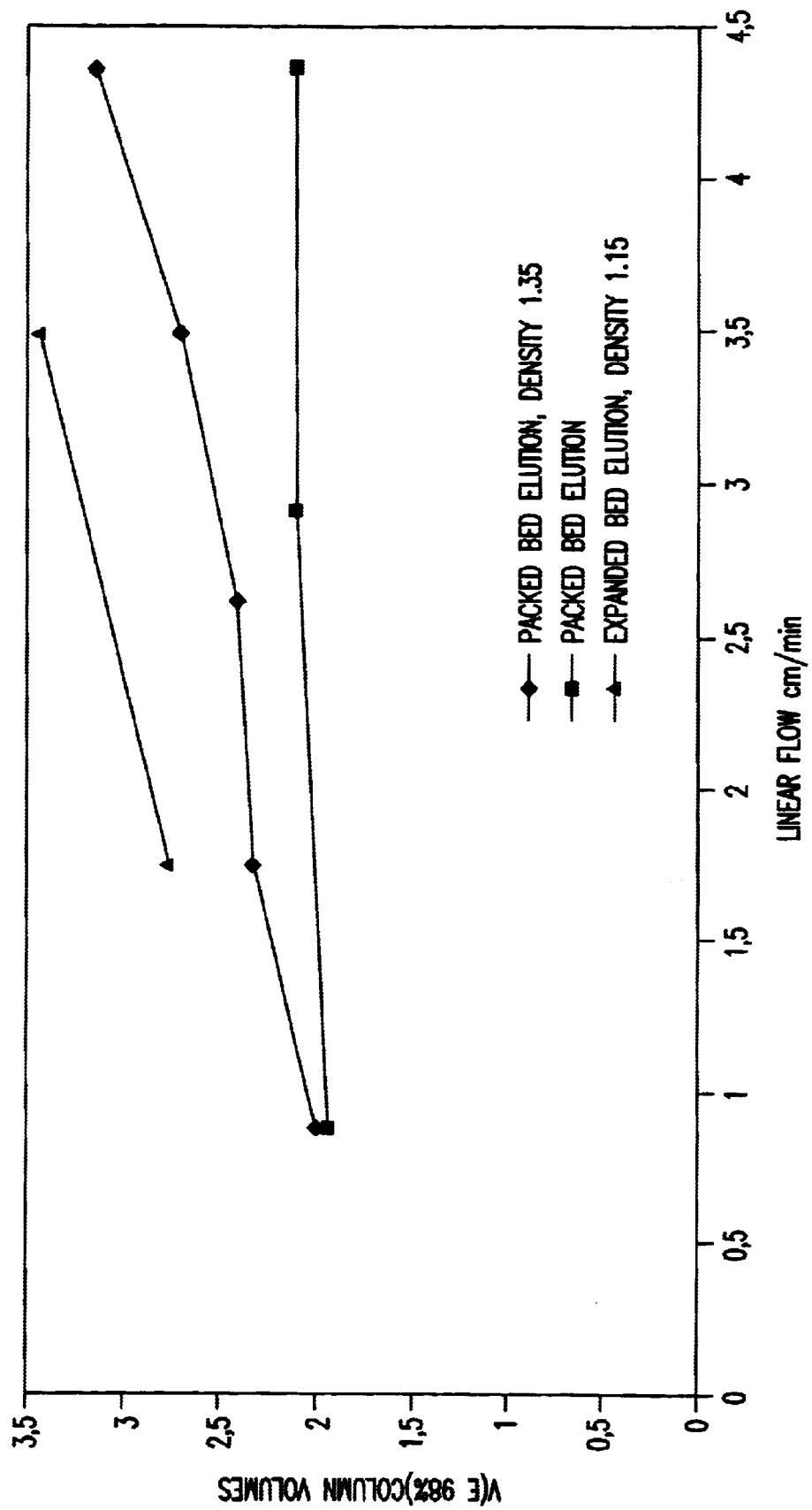

FIG. 13 shows the elution volume as a function of the linear flow rate at expanded mode and packed mode respectively.

FIG. A1 shows the expansion curves of three gels. $H/H_0$ was calculated as a function of the linear flow rate.

DESCRIPTION OF THE PREFERRED EMBODIMENTS

Hereinafter, a number of new initiatives and inventions will be presented individually. The purpose of all the inventions is to optimise and further develop the EBA technology. It should be understood that the individual elements may be used alone or in combination in connection with either the known EBA technology or the new All Expanded EBA technology.

The All Expanded Process

Previously in EBA, the standard was to elute the bound product in packed column, i.e. by means of elution from above and down. This is based on a wish to maximise the concentration of product in the eluate and minimise buffer consumption. Traditionally, the elution buffer is thus applied to a non-fluidised column of matrix (se above). There is an upper limit to the height of gel since it packs very hard already at low flow rates. In some cases, the limit is below 300 cm/min. See example 3. Gel is another term for matrix.

It has been surprisingly found that elution in fluidised mode leads to approximately the same buffer consumption, and that the concentration of the purified product in the eluate is by large the same as at elution in packed mode. Thus, the problem of hard packing of the matrix can be completely eliminated by elution in fluidised mode where elution occurs through a column of fluidised matrix particles. The invention is to elute in fluidised mode.

The new purification process can be described in steps as follows:

1. An adequate amount of chromatographic medium is placed in an EBA column.
2. A flow is initiated through the medium from below and up through the medium. The medium is fluidised.
3. The medium is rinsed in the column and the salt ion concentration and the pH are set.
4. The raw material is applied. The medium binds the target molecule.
5. Remaining raw material is rinsed out from the column.
6. The target molecule is eluted by the medium.
7. Rinsing and regeneration of the chromatographic medium (optionally).

it is surprising that all steps can be implemented in fluidised mode, i.e. Expanded Bed Mode.

The All Expanded Process of the present invention entails a material simplification of the EBA procedure and the matching apparatus (which will provide substantial economic savings) since all flows move in the same direction. During the entire purification process, the flow is one-way. It is not necessary to spend time packing the column and then draining it prior to elution. Elution in expanded bed according to the present invention can be initiated immediately after rinsing of the matrix.

Using the All Expanded Process of the present invention, elution can occur at rates of 0.1–100 cm/min. However, 2–20 cm/min is usually preferred and it is advantageous to elute at approximately 3–12 cm/min. These rates depend on the type of matrix used. The heavier the matrix, the greater rate during elution without too large expansion. By too large is meant that the matrix does not flow out of the column.

The All Expanded Process of the invention is recommended for the following expansion ratios: 1–5 times, advantageously 1.2–3 times, however 1.5–2 times is usually recommended. By expansion ratio is meant the relation between the volumes of the fluidised matrix and the sedimented matrix. See example 1 for a comparison of expansion curves of various density controlled media prepared by the applicant. The example shows a relation between expansion and flow of three media with different densities but with identical diameter (in the range of 100–300 $\mu$m). In the process different flow rates can be used. For example, it is often appropriate to rinse the matrix at a higher flow rate than the flow rate used for elution. This flexibility means that it is possible to economise time as operations at any time can take place at the optimal flow. The only problem is to hold the matrix inside the column. The heavier the matrix, the higher flow rate can generally be used.

The All Expanded Process of the invention can advantageously be applied by using a medium with a density of more than 1.2 g/ml, generally even more advantageously by using a medium having a density of more than 1,3 g/ml, and typically most preferably using a medium of more than 1,4 g/ml. By applying the present invention the flow rate of the elution step can in reality be varied freely which is a further advantage provided by the invention. Elution at high rates thus no longer represents a mechanical problem. This can economise time as it is possible by applying the All Expanded Process of the invention to elute faster and to elute a larger amount of matrix than it would be possible by eluting in a packed mode. The applicant recommends a matrix height of at least 20 cm.

As one of the major arguments for not eluting in the fluidised mode it has been mentioned that a greater volume of product is discharged than by conventionally packed elution, while at the same time consuming more buffer. However, it has been shown in a test series that the elution volume is closely related to the density of the chromatographic medium (see Example 2). The All Expanded Process of the invention thus allows to apply a matrix height which is in principle unlimited and thereby purifying a larger quantity of substance in each batch. Furthermore, the concern for a large elution volume is much exaggerated.

A further advantage of eluting in the fluidised mode is that the production costs of the column decrease on account of its simpler structure. There is no longer any need for an elution outflow at the bottom of the column or a supporting net for holding the matrix back. This opens the possibility of modifying (improving) the lower part of EBA-columns.

In the following a novel and simpler type of EBA-column will be described. See FIG. 3 for a construction example in principle.

FIG. 3 shows a possible construction without a supporting net or a distribution plate at the bottom. At the bottom, which could also be made to be self-discharging (i.e. having an opening allowing the discharge of the matrix material), there is only one opening which is used as an inlet for liquid fed to the column. Furthermore, it can be used for pumping matrix (gel) out and in. This is of major importance particularly in the case of large columns which it is not practicable to open at the top to adjust the matrix level. Above this inlet, the material is suitably stirred. In this new type of column there is thus no need for a supporting net or for a distribution plate. The much simpler structure of the column permits the use of a plurality of columns so as to provide an automated production arrangement yielding a continuous product flow.

The present invention therefore relates to a method for purifying target molecules from a mixture comprising the target molecules (e.g. proteins, immune globulins, BSA, enzymes, peptides, mono- or polyclonal antibodies, antigens, DNA, and plasmids, low molecular organic compounds) as well as impurity components (salts, solid particles which are at the least solid when applied to the column, etc.), the said method comprising:

a) establishing an Expanded Bed Adsorption column (either a known column or a column particularly prepared for expanded bed mode) comprising a particulate matrix material (see above examples of this), b) application of the mixture comprising molecular components and impurity components to the matrix material of the column, c) optionally rinsing the column in order to remove impurity components, d) eluting target molecules from the matrix material of the column, wherein the target molecules are eluted in expanded bed mode.

An adapted column will typically only comprise exactly one inlet and exactly one outlet. As described in the following an adapted all expanded column can advantageously apply magnetic stirring. Elution will preferably be made in expanded bed mode at a flow rate of 0.1–100 cm/min, e.g. 2–20 cm/min or 3–12 cm/min, and preferably at an expansion rate of 1–5, such as 1.2–3, e.g. 1.5–2 or 1.2–1.6. As mentioned, the density of the matrix material will typically be at least 1.2 g/ml such as at least 1.3 g/ml, e.g. 1.4 g/ml.

The present invention also relates to an EBA column which has been particularly adapted to elution in expanded mode.

Each of the elements of improvement to the novel type of column will be described in the sections below. It should be understood that the novel type of column may comprise one or more of these elements, some of which will be alternatives. It will also be understood that each of the elements of improvement may also be applied in conventional EBA systems and these elements therefore represent independent parts of the invention.

Magnetic Stirring in EBA Columns

Another way of obtaining a distribution of the inflowing liquids in EBA columns is by using magnetic stirring. This method is used for instance in fermentation tanks.

The application of the magnetic stirring of the invention in EBA columns makes it superfluous to provide a hole for a stirring shaft at the bottom of the column. This furthers production and eliminates the risk of a possible leak around this hole. Furthermore it eliminates the risk of growth of bacteria or the like in joints adjacent to this mechanical shaft. Furthermore this magnetic concept will be easier to sanitise. Non-filtrated liquid can still be pumped in above an optional supporting net. The magnetic stirrer is placed at the bottom, a loose magnet being placed inside the column and the motor outside. The motor can also be incorporated in the bottom piece itself. FIGS. 4 and 4a show examples of solutions comprising magnetic stirrers. FIG. 4 is a possibility available with the present column structure. In order to safeguard the supporting net, a wearing path may be provided. This should only be big enough to prevent the net from being unnecessarily worn. The path is a circle with a diameter of 10–100% of the diameter of the column, 30–50% being preferred. This wearing path is also to stabilise the rotation of the magnet. FIG. 4a takes the all expanded process of the invention into account and is thus constructed without a supporting net and with only one opening at the bottom. The magnet operates as a shut-off valve/plug, only at a flow coming in from below, the magnet is lifted. The wedge/cone-shape of the underside of the magnet also contributes to stabilising the magnet and preventing the magnet from suddenly coming off which could cause the destruction of the column. Stirring by shaft movement is replaced by magnetic stirring in EBA columns in the present invention.

In its simple embodiment where magnetic stirring is combined with the All Expanded Process of the invention, the supporting net and the outlet are eliminated, and the magnet may rest direct on the bottom of the column. However, a wearing path may still be installed in order to minimise the wear to the magnet and the bottom of the column and to control the movement pattern of the magnet.

The magnet and the wearing path are typically made of materials with a low friction such as polymers, particularly fluoropolymers, and especially polytetrafluoroethylene (PTFE), Teflon®. The shape of the magnet should be adapted so as to minimise the stirring zone.

Figure 5:
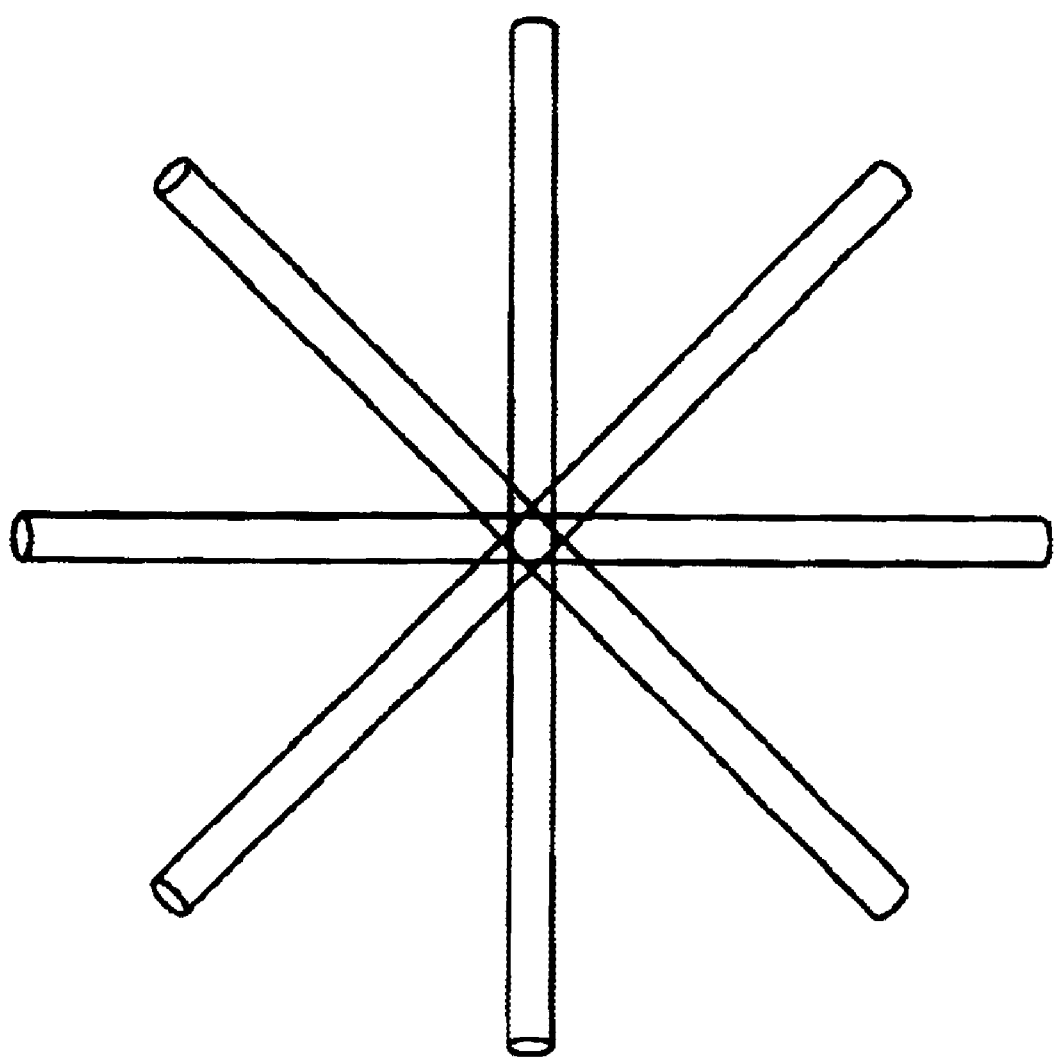

The motor to drive the magnet shall be able to drag the magnet at any time. This is related to the structure of the magnet. It may have 1–50 blades which are preferably placed symmetrically through the centre of the magnet. 1–20 blades is recommended, 1–8 blades being preferred. An example of a magnet is shown in FIG. 5. This is a planar drawing of the 8 blades. Other types and embodiments of magnets may also be applied.

The individual blades should have a shape to be easily sanitised and to reduce the stirring zone created by stirring.

The stirring zone will typically be 0–80% of the height of the fluidised matrix. However 1–50% is recommended, 1–15% being preferred. 1–10% is particularly preferred as a low stirring zone will have a favourable influence on the number of theoretical bottoms of the column. The magnetic stirring of the invention for EBA columns can be used in all sizes of EBA columns.

The present application therefore also applies to the use of magnetic stirring in an expanded bed adsorption purification process.

Design of an Inlet Ring with Multiple Openings

Using only one inlet makes it very difficult to distribute the inflowing liquid without increasing the stirring zone inappropriately. In connection with larger columns (a diameter larger than 20 cm) it can be difficult due to the localised inlet and the large diameter. The gel has to be lifted up in the entire column. The area of the inlet openings has to be controlled in order that they suit the individual column and the flow rate recommended thereto. In an EBA column a typical flow rate could be 6 cm/min. In a column with a diameter of 20 cm this corresponds to a flow of 18 ml/min. In this case, the linear flow from the four openings with a diameter of 3 mm each in an UpFront 20 EBA column will be 1600 cm/min/opening. If the same inlet openings were used in a column with a diameter of 40 cm where 6 cm/min=7.5 l/min, the linear flow would be 670,000 cm/min/opening. I.e. 440 times more. This means that the jet reaching the 40 cm column is much more powerful. This is inconvenient in connection with the distribution of the liquid and will entail the necessity of powerful stirring and thus a large stirring zone.

The inlet ring of the present invention designed with multiple openings increases the area of the inlet openings and at the same time distributes the inflow to a larger part of the column. This can be carried out by designing a ring which is located at the bottom of the column in a regular pattern. At the bottom of the column, an appropriate number of openings can be chosen. The number depends on the number necessary to lift the matrix in order to minimise stirring. 1–100 openings can be used, advantageously 4–40 and preferably 4–25. These numbers vary a lot since it also depends on the diameter of the opening and the column. The opening diameter may vary between 1–10 mm. See FIG. 6 and 7 for at possible construction and location of the inlet ring.

The inlet opening itself is directed inwardly in an angle of 0–80 degrees relative to the bottom of the matrix column. However, 0–30 degrees are recommended and 0 degrees are typically preferred, i.e. an opening in which the liquid jet is sprayed parallel to the bottom across the column. The pipe can also be embedded in the bottom part. It has been placed right at the side to avoid the presence of sedimented gel on the outer side. The outlet opening of the pipe is in line with the innerside of the column. The pipe is located completely outside the diameter of the column. The distance between two diagonal outlet openings is equivalent to the column diameter.

The pipe could also be constructed with a diameter which is smaller than that of the column. This inlet pipe would thus be provided with openings at both sides. Both to the centre and to the wall of the column. Two or more pipes, possibly concentric, would also be a possibility.

Thus, the application is also related to the use of a ring comprising multiple openings in an Expanded Bed Adsorption purification process.

Outlet at the Bottom or Side of the Column for the Discharge of Gel

When using large EBA columns, the discharge/filling of gel from/into the columns often causes problems. By the term large is understood columns for pilot production and above, usually with a column diameter of more than 5 cm, typically of more than 30 cm. This is solved by making an opening in the column for discharge and filling of the matrix. The matrix can be placed at the bottom or at the side just above a supporting net, if any. The outlet can be provided with a closing valve to turn on and off supply and discharge of matrix. The matrix has to be fluidised to be able to flow out.

In practice this is carried out as follows:

After the final rinsing of the matrix, the valve is opened and the flow is stopped. The matrix will sediment while flowing out. If it packs and thus clogs the opening, the outlet opening should be bigger. Another solution is to close the valve and fluidise the matrix again and continue to do so until the matrix is out. The opening may have a diameter of 1–100% of the column diameter. However, 10–40% is recommended. If a column without a supporting net is used, All Expanded Process, the bottom can be made to be self-discharging and the outlet can advantageously be placed here.

Mobile Pipe Outlet

On application of EBA technology large quantities of liquid are used. These can be reduced by using the above mentioned element of the invention. Reducing the buffer volume leads to economic savings. The buffer can be used for rinsing, elution or regeneration. The idea is to reduce the headspace, i.e. the height of the liquid above the matrix, and since the matrix has different heights in the various processes the pipe outlet has to be mobile. Advantageously, the headspace can be reduced, since a mix of the different fluids occurs here.

Instead of the Fixed Outlet at the Top of the Columns Produced by e.g. UpFront

Chromatography A/S, Denmark, a mobile (variable) outlet can be used. It consists of a pipe which can be adjusted up and down in the column depending on the level of the liquid front (see FIG. 8). This can be done both manually and automatically. For instance by means of hydraulics or rubber wheels which can mechanically move the pipe up and down. These rubber wheels must be of a suitable material which are not deposited on the pipe. As the tolerance between the pipe outlet and the column is not critical, the mobile pipe outlet of the invention is inexpensive to produce and in addition a simple solution.

The pipe outlet makes it possible to reduce head space throughout the entire EBA process. This adjustable pipe outlet may/has to be combined with an air valve at the top of the column. Thus, it can suck out and pump in air as well as create an overpressure or a negative pressure relative to the surroundings. In this manner, it can be ensured that the liquid height will not rise above the pipe outlet during purification procedures.

The pipe can be of a length corresponding to the column length. It can be made of a material which does not leak anything to the various fluids used in EBA technology. Acid-resistant stainless steel with a fine polishing can be used. The diameter may vary and should be adjusted according to the column diameter. If a too small outlet is chosen, pressure in the air space above the liquid will rise which could pose a problem. On misapplication, the pipe outlet will act as a vacuum cleaner, making a reversed vortex and possibly sucking out the matrix, even though the distance from the pipe opening and the matrix height is more than 10 cm. Therefore, it is important that the pipe outlet has a suitable diameter. If the pipe diameter becomes to large, the mobile pipe outlet of the invention is not relevant since the head space is not reduced if the pipe has a large volume. A diameter of 1–50% of the column's diameter can be used, however pipes with a diameter of 5–30% are recommended, but preferably 8–20%. The pipe itself extends down through the top of the column through an opening with approximately the same diameter as the pipe. On the outer side of the top an O-ring of a suitable material is fixed around the pipe. When the O-ring is pressed against a special conical device, it is pressed against the pipe and this device, thus obtaining pressure stability around this opening in the column. See FIG. 8 for the fundamental construction and location of a mobile pipe. Here, an EBA column in which elution in packed mode can occur is shown. In principle, the construction is not essential to the invention, however the UpFront float becomes redundant when the pipe is constructed in the manner shown. At the end of the pipe, a small plate which will ensure a gentle and good distribution of elution buffer during packed elution is placed. The pipe does not necessarily have to be located at the middle of the column. Advantageously, the pipe outlet can be used in both a packed and fluidised column.

The pipe can also be used to discharge gel from the column by closing all bottom valves and pumping air through the air valve at the top so as to press liquid and matrix through the pipe which in this case will be the only way out. Naturally, this requires that the column can manage an overpressure of approximately 0.1–1.0 bar.

Floating Outlet

On application of the EBA technology large quantities of liquid are used, however these can be reduced by using the invention. Reducing the buffer volume leads to economic savings. The idea is to reduce head space, the height of the liquid above the matrix. As the matrix has different heights during the various processes, the outlet has to be mobile.

Figure 9A:
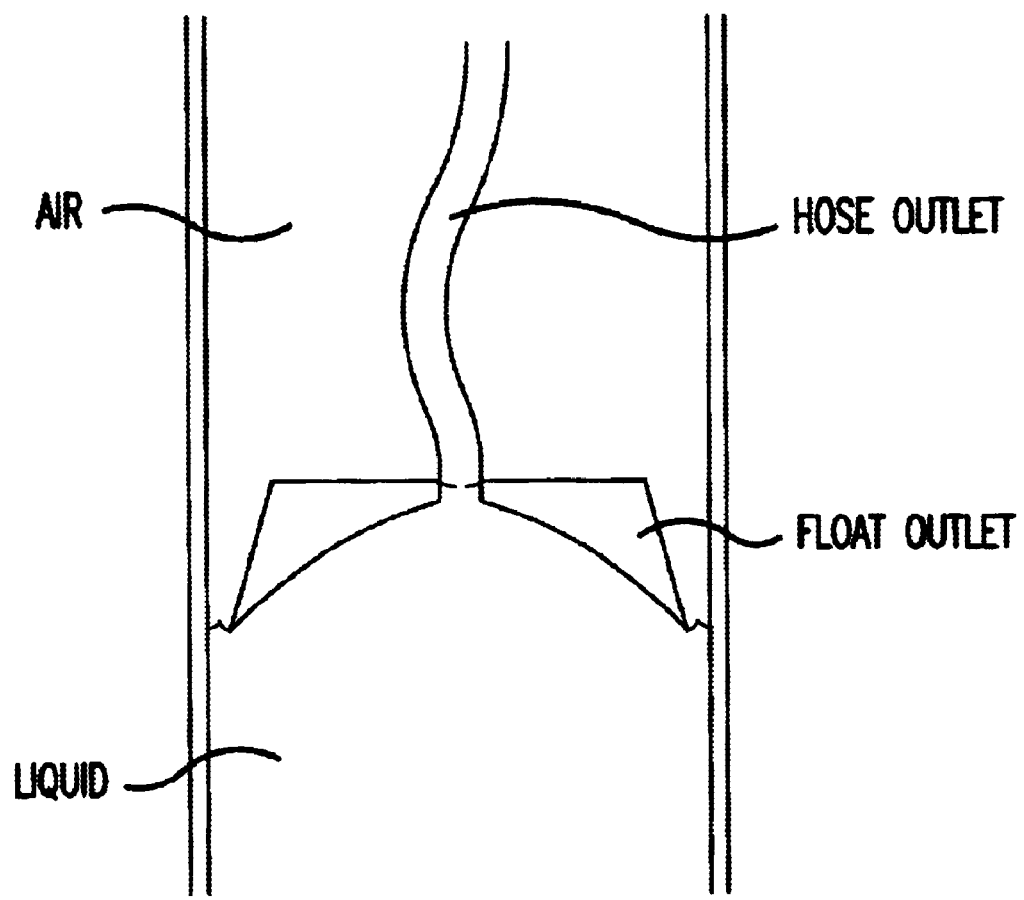

The floating outlet of the invention has the same purpose as the pipe outlet. Here, the idea is that a socalled floating outlet floats on the liquid surface. By such an outlet is understood a floating outlet made of a material which permits it to float. It follows the liquid surface during the different steps of the EBA purification process. The diameter may vary from 1–99.9% of the column's diameter. However, 50–99.9% is recommended. The floating outlet can be constructed to be assembled of two parts in order to make it hollow inside. This opens up the possibility of filling it up with a material of another density so as to adjust the total density to the liquid on which it is intended to float. At the underside of the floating outlet is an opening which is formed so as to avoid "dead pockets". In such, air and matrix could be trapped, however, this is avoided and sanitary validation is thus easier. See FIG. 9 for an example. Here, a cross section of a possible construction of the floating outlet (FIG. 9a) is shown. The floating outlet is mounted with a hose to the top of the column where liquid can flow out of the column. This hose may have various diameters and must have a length which does not prevent the movement of the floating outlet in the entire column. Advantageously, the opening and the hose may have the same diameter as the inlet pipe. Thus, this will not create a further pressure drop. The floating outlet can be used in both fluidised and packed mode. This floating outlet can be combined with a valve at the upper part of the column. Through this pressure can be adjusted. Thus, it can suck out air and pump in air as well as create an overpressure or a negative pressure relative to the surroundings. In this manner, it can be ensured that the liquid height will not rise above the floating outlet during purification procedures. This valve is not shown in FIG. 9. It is shown in FIG. 8. The floating outlet can not, as the pipe outlet, be moved into the matrix and therefore it can not normally be used to discharge gel from the column.

Temperature Regulator at Inlet

The purified substances are often more stable at low temperatures, e.g. 2–4° C. At this temperature interval the viscosity of the liquid is usually larger and the capacity and productivity of the matrix are thus smaller. In addition, the bond effectiveness is normally reduced at low temperatures. By using a temperature regulator at the inlet of the column, the effects of all these factors can be reduced.

At all inlets of the column a thermometer and a thermostat or a cooling/heating unit are installed to control the temperature of all fluids being pumped into the column. The cooling/heating unit could consist of a pipe heat exchanger or a plate heat exchanger. A connected control unit may control the temperature of the inflowing fluids at all times. This can be advantageously as regards time since the chromatographic medium has a larger capacity at higher temperatures. In this manner, particularly temperature sensitive purifications can be controlled by means of this concept. The temperature regulator can be manually controlled or be automated by a computer. An in-line installation is also possible. The raw material can remain in a cold store and be pumped directly through the in-line temperature regulator and through the EBA column for purification purposes.

Additionally, the purified product can be cooled immediately after elution by means of a corresponding temperature regulator at the outlet.

Coloured Gel

In EBA technology it is possible to pump often very impure and unclear raw materials into a column. This means that it becomes very difficult to see the matrix in the column. By using coloured gel the extent to which the matrix has expanded can be seen at any time.

If the matrix is given an appropriate colour, the expansion can be seen. The matrix can obtain this colour in three ways:
1) The matrix is constructed in such a manner that under certain conditions, e.g. pH, salt concentration or temperature, it possesses a colour which is different from that of the raw material.
2) A colorant is bound to the active matrix. Two examples may be Reaktive black 5 (Sigma product no.R6506) and Reaktive Red 8 (Aldrich no. 24.482-1).
3) A given percentage of a coloured inactive matrix is mixed with the active. 0.1–100% can be mixed into the active gel, preferably 5–10%.
4) A given percentage of the active matrix is coloured. From 0. 1–100% of the active gel can be coloured, preferably 5–10%.

The colorants are covalently bound to the gel which makes the binding stable.

It is important that the chosen colour does not cause problems which will affect the individual steps of the EBA process.

In addition, the present invention relates to the use of a coloured gel in an Expanded Bed Adsorption purification process.

Sensor

On application of EBA technology large quantities of liquid are used. These can be reduced by applying a sensor to the outlet. Reducing the quantity of liquid leads to economic savings. The idea is to control the size of head space, the expansion, flow rate and stirring.

A sensor detecting the distance between the liquid surface and the expanded matrix can be used to calculate the degree of expansion. The sensor may be fixed either at the top of the column or to one of the two above-mentioned mobile outlets. The sensor itself may be an ultrasound or colour sensor or another known type to solve the task. The information from the sensor can be handled manually or by a computer receiving information about matrix and liquid height continually. Based on pre-programmed data this computer controls that the correct expansion is maintained and that the ratio between matrix height and liquid height is maintained. In this manner, the entire purification procedure can be automated and controlled by means of computers and purification can be controlled automatically. This facilitates the operation of EBA column systems. The sensor of the invention opens the possibility of producing columns of materials which are not translucent, transparent. A coloured matrix opens the possibility of using a colour sensor to control expansion.

Regeneration of Buffer in EBA Systems

If the consumption of buffer in large-scale purification is reduced, it leads to a material reduction of production costs. On application of a system according to the invention, a large part of the buffer liquid can be recirculated. In addition, reducing buffer consumption is environmentally advantageous.

FIG. 10 shows the regeneration of a large quantity of buffer during the steps of rinsing and regeneration. That is the steps before and after the raw material is applied and during elution. The system of FIG. 10 entails the application of the buffer liquid after passage through the column and three monitors to an in-line ultra filtration (reversed osmosis can also be applied). During ultra filtration the high-molecular substances will be separated from the liquid which will then flow through an in-line pH/salt ion concentration regulator. In this the desired pH and salt ion concentration is set. Then, the buffer is led back to the tank to be pumped through the column again. Some of the liquid is reused. However, some is lost with the high-molecular substances.

FIG. 10A shows the regeneration of a large quantity of buffer during the elution step. That is the step during which the target molecule is "released" of the matrix. The system of FIG. 10A entails the application of the elution buffer after passage through the column and three monitors to an in-line ultra filtration (reversed osmosis can also be applied). During ultra filtration the target molecule will be separated (the target molecule is a high-molecular substance). The target molecule is passed on through a micro filter which is a coarser filter permitting the target molecule to pass for further purification and retaining e.g. bacteria. The liquid flowing through the ultra filter is led through the in-line pH/salt ion concentration regulator. In this the desired pH and salt ion concentration are set. Then, the elution buffer is led back to the tank to be pumped through the column again. Some of the liquid is reused. However, some is lost with the target molecule/high-molecular substances.

The regeneration of buffer in EBA systems according to the invention may be used in the present EBA systems and in the All Expanded Process of the invention. Ultra filtration is preferred to reversed osmosis since a large part of the salt ions retained during reversed osmosis is lost during this process. This results in additional expenses for e.g. salts. Using ultra filtration, both water and salt consumption can be reduced. Buffer solutions are typically weak salt solutions. One example of an elution buffer could be 0.5 M NaCl set to pH=7.0. A washing buffer could be 0.01 M dipotassiumhydrogenphbsphate set to pH=7.0.

Baffles

During stirring, part of the fluidised matrix will constitute the stirring zone which is important for the number of theoretical bottoms in the column. On application of a column with baffles, the stirring zone can be reduced with no reduction of the stirring efficiency in order that the number of theoretical bottoms (and thus the efficiency of the column) is increased.

To reduce the stirring zone baffles can be inserted. By the term baffles is understood items of different sizes which may be inserted on the innerside of the column. Preferably, they will be placed at the lower part of the column. The number of baffles may be varied.

Disposable Columns

The biological and pharmaceutical industries use many resources to validate systems. That is they ensure that all equipment fulfil certain predetermined requirements. On application of EBA columns, the matrix and the column have to be validated after each production and regeneration. By using disposable columns this expensive process can be eliminated.

Disposable columns for specific purification tasks may be produced. The column with its contents can be guaranteed to meet the requirements demanded by the individual purification process. Thus, the producer and not the customer will carry out validation. The in/outlets of the column are sealed. The seal is only broken when the column has been placed at the site of use. A valve coupling can e.g. be fixed across a sealing and thereby break it. "Plug and use".

The columns may be made of moulding plastic which minimises production costs. The design/construction of the individual columns will correspond to the ones previously described. For instance as FIG. 3. Advantageously, the stirring could be replaced by a magnetic stirrer in order to make the column more sterile. In addition, a floating outlet having a sensor would be a good supplement. The column may be cast without a top. The matrix in a 20% spirit solution is poured in, the floating outlet is positioned and the top is welded thereto. There is no air inside the column. It is completely filled up with the spirit solution. The sedimented matrix height depends on the use of the disposable column. Disposable columns may be used in laboratory scale and up to production scale.

The consumer has all the necessary, re-usable equipment such as pumps, hoses/pipe systems, coupling valves, possibly a magnetic stirrer or another stirring unit and computer control. Only the disposable column and its contents is replaced quickly and easily after use. This means that the consumer does not have to regenerate and then validate the column after use, a new is simply installed.

Once the mould for casting the individual column has been made, only small changes are necessary in order to offer many consumers a very inexpensive EBA column which can be used several times in many situations. The matrix can be replaced and supplied for the individual purification tasks. In stead of welding the top onto the matrix, it can be modified so as to make it possible to remove and fix it and thereby replace the matrix. At first sight, this seems to be a bad bargain but if the core business is selling matrixes, it makes sense. Now, the consumer can buy a cheap column and soon begin the EBA process. This is another argument in favour of choosing EBA rather than other purification methods.

The present application also relates to a complete Expanded Bed Adsorption column comprising a cylindrical column wall having a first end and a second end; a bottom part connected to the first end of the cylindrical column; a top part connected to the second end of the column; a particulate matrix material, said matrix material being located in the column surrounded by the column wall, the bottom part and the top part; at least one bottom opening in the bottom part or at the end of the column wall adjacent to the bottom part; and at least one top opening in the top part or at the end of the column wall which is adjacent to the top part.

The ratio of the axial length of the column wall to the inner cross-sectional diameter of the column wall is 100:1 to 2:1, such as 60:1 to 4:1, e.g. 40:1 to 10:1 or 15:1 to 5:1.

In an interesting embodiment the column wall is made of plastic, e.g. moulding plastic. In addition, it is advantageous that the column wall, bottom part and top part are made of one piece of material, preferably of plastic.

In a particularly interesting embodiment the top opening (s) and the bottom opening(s) are sealed by a seal which has to be broken before the column is used. As mentioned, this construction enables the matrix material to be sterile which is interesting particularly in a medical applications.

In another interesting embodiment which may be combined with the above-mentioned embodiments, the column further contains a magnetic stirring body embedded in the column material adjacent to the bottom part. During packing of the completed column, it must be ensured that the magnet is placed close to the bottom part in order to initiate stirring immediately on fluidisation of the matrix material.

It is advantageous if the matrix material fills $1/3$ to 1.2, such as $1/3$ to $1/1.2$, preferably $1/2$ to $1/1.5$, of the volume constituted by the column wall, the bottom part and the top part.

Additionally, the column may contain a float adapter placed between the column material and the top part. The diameter of the float adapter is typically 50–99.9% of the diameter of the cylindrical column wall and the height of the float adapter is typically from $\frac{1}{100}$ to $\frac{1}{10}$, e.g. $\frac{1}{50}$ to $\frac{1}{15}$, of the axial length of the column wall. Preferably, the column is substantially gas free, where a storage buffer, e.g. an aqueous ethanolic solution, occupies the volume.

The application of one sphere in the sphere in packed column chromatography. When a packed column is applied in the purification of proteins and peptides, the particles used at present are not particularly pressure stable. See example 3. Furthermore there is a limit to how fast a liquid flow can be provided before the column packs down hard and the liquid has difficulties running through; this limit being between 200–300 cm/hour. The said problem is solved by applying one sphere in the sphere in packed column chromatography.

Figure 11:
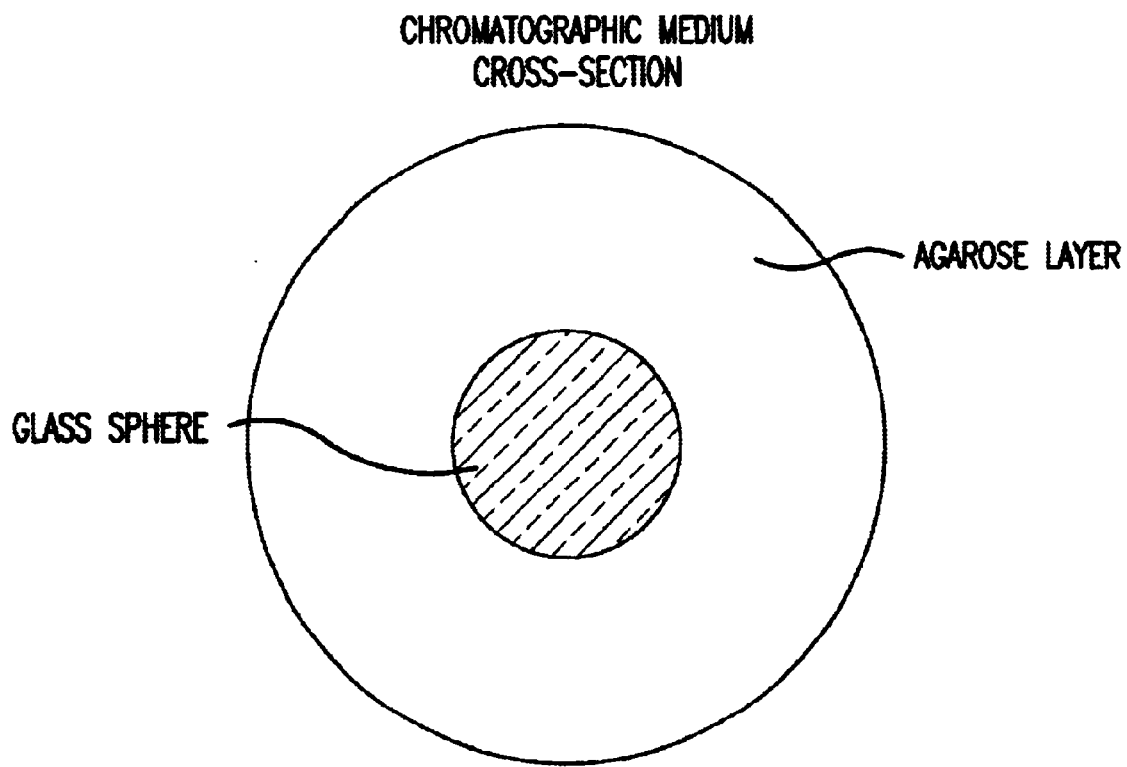

By applying one sphere in the sphere particles in packed column chromatography a higher pressure stability is obtained. This means that it is possible to elute at a higher rate before the column packs down hard and cuts off the flow. Example 3 shows that it can be an advantage to apply one sphere in the sphere in packed column chromatography, as this provides high mechanical stability enabling greater flow and/or greater columns. Greater gel height in a packed column. Furthermore, one sphere in the sphere in packed column chromatography gives a shorter diffusion path. By the term one sphere in the sphere is meant a chromatographic sphere inside which has been cast an inert impermeable particle. FIG. 11 shows a section of a chromatographic medium for use in the packed mode. This shows such a sphere cast in agarose or another polymer material.

The relationship between inert impermeable sphere(s) and the chromatographic medium can be varied; 1–90 volume % inert impermeable sphere, 5–50 volume % inert impermeable sphere being recommended, 10–30 volume % inert impermeable sphere being preferred. The diameter of the entire sphere can be varied in the range of 10–1000 $\mu$m, 30–500 $\mu$m being recommended, 35–300 $\mu$m being preferred, and 40–100 being particularly preferred. The pore size of the chromatographic material may be varied so as to make it possible for the required target molecule to enter the sphere.

Examples of Particularly Preferred Spheres:

The chromatographic material is agarose, and glass is used for inert impermeable spheres.

Diameter of the entire sphere: 40–100 $\mu$m. Glass content: 2–40% or 5–25%.

Diameter of the entire sphere: 30–200 $\mu$m. Glass content: 2–40% or 5–25%.

The present application therefore also relates to the use of sphere-in-sphere matrix particles in packed column chromatography. Such matrix particles are composed of e.g. glass spheres individually coated with a substantially uniform layer of agarose, such as UpFront agarose spheres from UpFront Chromatography A/S, Denmark.

EXAMPLES

Example 1

Expansion Curves Determined for Three Gels of Different Densities.

The three tested matrices are:

Amersham Pharmacia Biotech, Sweden: Streamline Deae with density 1.15 g/ml

UpFront Chromatography A/S, Denmark, Deae matrix density 1.35 g/ml

UpFront Chromatography A/S, Denmark, Deae matrix density 1.60 g/ml

All three were DEAE activated matrices with diameters between 100 and 300 $\mu$m.

The test was made with a packed gel height of 20 cm ($H_0$). Water was pumped through the gel, and the gel height H was registered at different velocities at a stable expansion. $H/H_0$ was calculated and is shown in FIG. A1 as a function of the linear flow rate.

Conclusion

At higher density of the chromatographic medium higher flow rate can be implemented without further expansion of the matrix. If the flow rate is increased, the density of the medium should also be increased (provided that the diameter remains constant).

Example 2

Selected Results From a Number of Elution Tests.

Three different matrices with different densities were used.

Amersham Pharmacia Biotech, Sweden: Streamline Deae with density 1.15 g/ml

UpFront Chromatography A/S, Denmark, Deae matrix density 1.35 g/ml

UpFront Chromatography A/S, Denmark, Deae matrix density 1.60 g/ml

All three were DEAE activated matrices with diameters between 100 and 300 $\mu$m.

Description of the test:

1000 g of matrix is rinsed on absorption filter using:

1. ion exchanged water 4 l
2. 0.1 M $K_2HPO_4$, pH=7.0, consumption 4 l
3. 10 mM $K_2HPO_4$, pH=7.0, consumption 4 l BSA buffer (2 mg/ml in 10 mM $K_2HPO_4$, pH=7.0) is prepared. 10 ml of BSA buffer/g gel should be used, i.e. 10 l per 1000 g matrix. The matrix is stirred in this buffer for 2 hours at room temperature. The matrix binds the target BSA molecule. The resulting product is then rinsed on a suction filter using 10 mM $K_2HPO_4$, pH=7.0, consumption 5 l.

65 g is placed in an UpFront 20™ expanded bed column. The matrix is fluidised therein once with 10 mM $K_2HPO_4$, pH=7.0, before initiation off the elution.

A. Test series eluting in a packed column. Packed mode.

B. Test series eluting in a fluidised column. Packed mode.

A and B are performed at the same flow rate. Eluting buffer is 20 mM $K_2HPO_4$ in 0.5 M NaCl, pH=7.0.

Subsequently, $V_{E90}$, being the volume at which 90% of the target molecule leaves the outlet is calculated. The results are shown in Table 1.

TABLE 1

| | Density | V<sub>E90</sub> |
|---|---|---|
| Streamline | 1.15 g/ml | 208 ml |
| UpFront matrix | 1.35 g/ml | 118 ml |
| UpFront matrix | 1.60 g/ml | 96 ml |

The following results show that elution in fluidised mode yields a smaller elution volume if density increases over and above a certain value (see Table 2).

TABLE 2

| | Elution rate | $V_{E90}$ |
|---|---|---|
| Packed mode | 104 cm/min | 251 ml |
| Fluidised mode | 104 cm/min | 90 ml |

Table 2 compares two UpFront matrices having the density 1.60 g/ml. The same test conditions as described above were applied. This time elution was performed in two different modes.

Example 3

Elution tests were made using an EBA ion exchanger of the DEAE type (UpFront EBA matrix, density about 1.35).

Purified bovine serum albumin was bound to 1 liter of DEAE ion exchanger by batch incubation at pH 7 (20 mg of BSA/ml matrix). The DEAE ion exchanger was divided into 65 ml portions which were eluted successively one by one in either packed bed mode or in expanded bed mode. The elution experiments were even made at different flow rates. All experiments were made using an UpFront EBA-column (Ø=2 cm)—see FIG. 8.

FIG. 12 shows a typical UV profile obtained as a result of the elution experiments. A linear flow rate of 1 cm/min was used both in the packed bed and the expanded bed elutions.

FIG. 13 shows the elution volume (defined as the volume of the fractions between the start of the elution peak and the point where 98% of BSA has been eluted ($V_{E\ 98\%}$)) as a function of the linear flow rate. The elution volume is expressed in relative terms compared with the (packed bed) volume of the matrix material.

The experiment shows that expanded bed elution does not cause any significant rise in elution volume as long as the linear flow rate is in the range of about 1–3 cm/min. At higher flow rates a major increase in the elution volume will probably be found.

Example 4

Packed column chromatography. Pressure stability of matrix with and without one glass sphere in the sphere.

A) 6% UpFront agarose spheres, diameter 80–150 μm without glass, in Pharmacia FPLC column 10 mm Ø, 10 cm matrix

TABLE 3.1

| Flow rate cm/hour | Press. atm |
|---|---|
| 50 | <0.5 |
| 100 | <0.5 |

TABLE 3.1-continued

| Flow rate cm/hour | Press. atm |
|---|---|
| 200 | <0.5 |
| 300 | >30.0 |

B) 6% UpFront agarose spheres, diameter 80–150 μm with glass, one sphere in the sphere (20% w/v) in Pharmacia FPLC column 10 mm Ø, 10 cm matrix

TABLE 3.2

| Flow rate cm/hour | Press. atm |
|---|---|
| 150 | <0.5 |
| 600 | <0.5 |
| 2000 | 0.5 |
| 3000 | 1.0 |
| 4000 | 2.5 |

Conclusion

It was found advantageous to use one sphere in the sphere for packed column chromatography, as this provides high mechanical stability enabling higher flow and/or larger columns. Greater gel height in packed column. Furthermore, one sphere in the sphere in packed column chromatography gives a shorter diffusion path.

What is claimed is:

1. A method for the purification of target molecules from a mixture comprising the target molecules and impurity components while minimizing elution butter consumption, said method comprising:

a) establishing an Expanded Bed Adsorption column comprising a particulate matrix material having a density of at least 1.2 g/mL, b) application of the mixture comprising molecular components and impurity components to the matrix material of the column, c) optionally rinsing the column in order to remove impurity components, and d) eluting the target molecules from the matrix material of the column, at a flow rate of 2–20 cm/min keeping the expansion ratio matrix material within 1.2–3, wherein the eluting of the target molecules is performed in expanded bed mode.

2. A method according to claim 1, wherein the density of the matrix material is at least 1,3 g/ml.

3. A method according to claim 2, wherein the density of the matrix material is at least 1,4 g/ml.

4. A method according to claim 1, wherein the elution in expanded bed mode is performed at a flow rate 3–12 cm/min.

5. A method according to claim 1, wherein the elution in expanded bed mode is performed at an expansion ratio of 1.5–2.

6. A method according to claim 5, wherein the elution in expanded bed mode is performed at an expansion ratio of 1.2–1.6.

* * * * *